(12) United States Patent
Inoue et al.

(10) Patent No.: US 9,461,252 B2
(45) Date of Patent: *Oct. 4, 2016

(54) ORGANOMETALLIC COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Tomoka Nakagawa, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 132 days.

This patent is subject to a terminal disclaimer.

(21) Appl. No.: 14/447,906

(22) Filed: Jul. 31, 2014

(65) Prior Publication Data

US 2014/0339533 A1 Nov. 20, 2014

Related U.S. Application Data

(63) Continuation of application No. 13/191,665, filed on Jul. 27, 2011, now Pat. No. 8,795,851.

(30) Foreign Application Priority Data

Jul. 28, 2010 (JP) ................................. 2010-169868

(51) Int. Cl.
*H01L 51/00* (2006.01)
*H01L 27/32* (2006.01)
(Continued)

(52) U.S. Cl.
CPC ....... *H01L 51/0085* (2013.01); *C07F 15/0033* (2013.01); *C09K 11/06* (2013.01); *H01L 27/32* (2013.01); *H01L 51/5012* (2013.01); *H01L 51/007* (2013.01); *H01L 51/0074* (2013.01)

(58) Field of Classification Search
CPC . H01L 27/32; H01L 51/007; H01L 51/0074; H01L 51/0085; H01L 51/5012; C09K 11/06
See application file for complete search history.

(56) References Cited

U.S. PATENT DOCUMENTS 7,648,778 B2 1/2010 Igarashi et al.
7,807,839 B2 10/2010 Inoue et al.
(Continued)

FOREIGN PATENT DOCUMENTS

EP 1 777 229 A1 4/2007
JP 2006-060198 A 3/2006
(Continued)

*Primary Examiner* — Dawn Garrett
(74) *Attorney, Agent, or Firm* — Husch Blackwell LLP

(57) ABSTRACT

An object is to provide a novel organometallic complex that has a broader emission spectrum in the wavelength range of green to blue. Other objects are to provide a light-emitting element using the organometallic complex, and a light-emitting device, an electronic device, and a lighting device each using the light-emitting element. Provided is an organometallic complex represented by a general formula (G1). Represented by the general formula (G1) is a novel organometallic complex that exhibits a broad emission spectrum in the wavelength range of green to blue. Further provided are a light-emitting element using the organometallic complex, and a light-emitting device, an electronic device, and a lighting device each using the light-emitting element.

15 Claims, 17 Drawing Sheets

(51) Int. Cl.
*H01L 51/50* (2006.01)
*C09K 11/06* (2006.01)
*C07F 15/00* (2006.01)

(56) References Cited

U.S. PATENT DOCUMENTS

| | | |
|---|---|---|
| 8,795,851 B2 | 8/2014 | Inoue et al. |
| 2011/0101854 A1 | 5/2011 | Inoue et al. |
| 2011/0260145 A1 | 10/2011 | Omary |
| 2011/0282059 A1 | 11/2011 | Baranoff et al. |
| 2012/0025177 A1 | 2/2012 | Yoon et al. |

FOREIGN PATENT DOCUMENTS

| | | |
|---|---|---|
| JP | 2007-081388 A | 3/2007 |
| JP | 2007-137872 A | 6/2007 |
| JP | 2008-069221 A | 3/2008 |
| JP | 2009-013366 A | 1/2009 |
| JP | 2012-517422 | 8/2012 |
| JP | 5738699 B2 | 6/2015 |
| WO | WO 2010/089394 A1 | 8/2010 |
| WO | WO 2010/090362 A1 | 8/2010 |

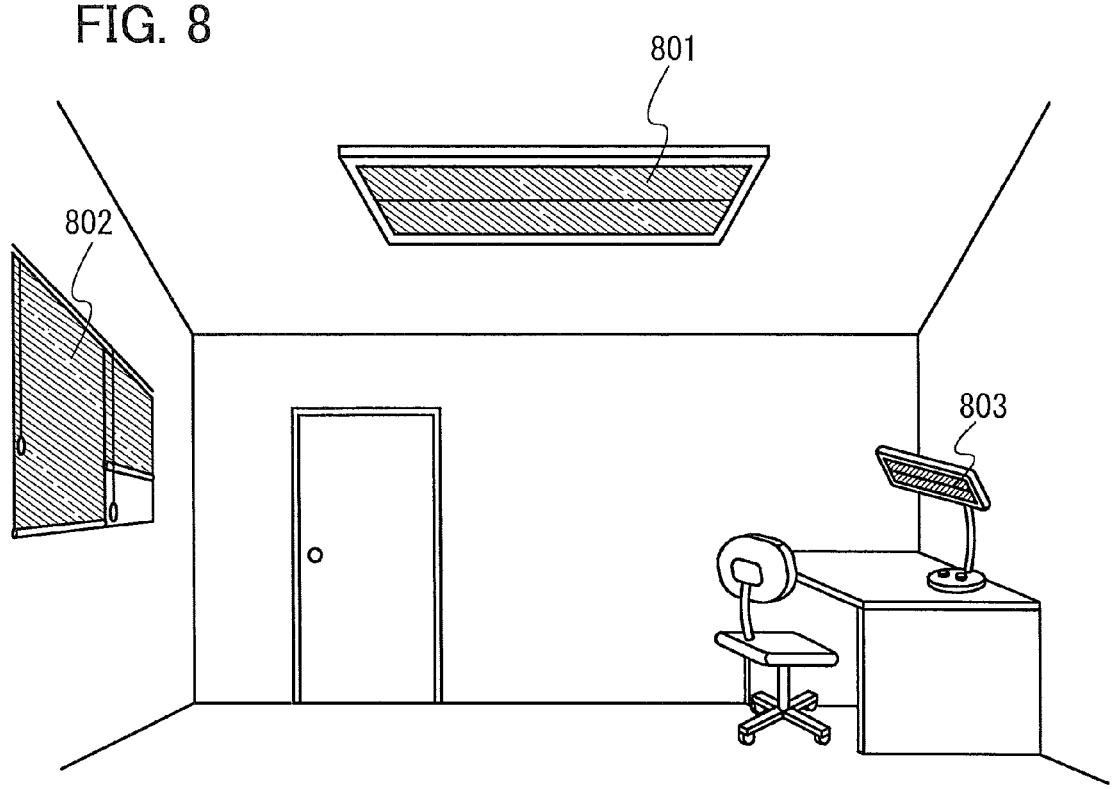

ORGANOMETALLIC COMPLEX, LIGHT-EMITTING ELEMENT, LIGHT-EMITTING DEVICE, ELECTRONIC DEVICE, AND LIGHTING DEVICE

This application is a continuation of copending U.S. application Ser. No. 13/191,665, filed on Jul. 27, 2011 (now U.S. Pat. No. 8,795,851 issued Aug. 4, 2014) which is incorporated herein by reference.

BACKGROUND OF THE INVENTION

1. Field of the Invention

The present invention relates to an organometallic complex. In particular, the present invention relates to an organometallic complex that is capable of converting a triplet excited state into luminescence. In addition, the present invention relates to a light-emitting element, a light-emitting device, an electronic device, and a lighting device each using the organometallic complex.

2. Description of the Related Art

In recent years, there has been an active development of light-emitting elements in each of which an organic or inorganic compound having a light-emitting property is used as a light-emitting material. In particular, a light-emitting element called an EL (electroluminescence) element has attracted attention as a next-generation flat panel display element because it has a simple structure in which a light-emitting layer containing a light-emitting substance is provided between electrodes, and characteristics such as feasibility of being thinner and more lightweight and responsive to input signals and capability of driving with direct current at low voltage. Moreover, a display using such a light-emitting element has high contrast, excellent image qualities, and a wide viewing angle. Furthermore, such a light-emitting element is a planar light source, and accordingly its applications to light sources, such as backlights of liquid crystal displays and lighting, have been under contemplation.

In the case where the light-emitting substance is an organic compound having a light-emitting property, the emission mechanism of the light-emitting element is a carrier-injection type. Specifically, by application of a voltage to electrodes between which the light-emitting layer is interposed, electrons and holes injected from the electrodes recombine to raise the light-emitting substance to an excited state, and light is emitted when the substance in the excited state returns to the ground state. Possible excited states are a singlet excited state (S*) and a triplet excited state (T*). In addition, the ratio of S* to T* fainted in the light-emitting element is statistically considered to be 1:3.

In general, the ground state of an organic compound having a light-emitting property is a singlet state. Luminescence from a singlet excited state (S*), which is electron transition between the same multiplicities, is called fluorescence, and luminescence from a triplet excited state (T*), which is electron transition between different multiplicities, is called phosphorescence. At room temperature, observations of a compound which emits fluorescence (hereinafter referred to as a fluorescent compound) usually show only fluorescence without phosphorescence. Thus, the internal quantum efficiency (the ratio of generated photons to injected carriers) of a light-emitting element using a fluorescent compound is assumed to have a theoretical limit of 25% based on a S*-to-T* ratio of 1:3.

On the other hand, by use of a phosphorescent compound, the internal quantum efficiency can be increased to 75% to 100% in theory. In other words, an element using a phosphorescent compound can have three to four times as high emission efficiency as that of an element using a fluorescent compound. For these reasons, a light-emitting element using a phosphorescent compound has been actively developed in recent years in order to achieve a highly-efficient light-emitting element. As the phosphorescent compound, organometallic complexes that have iridium or the like as a central metal have particularly attracted attention because of their high phosphorescence quantum yield: for example, an organometallic complex that emits light in the wavelength range of green to blue is disclosed as a phosphorescent material in Patent Document 1.

REFERENCE

Patent Document

Patent Document 1: Japanese Published Patent Application No. 2007-137872

SUMMARY OF THE INVENTION

However, not many reports have been made of phosphorescent materials that emit green or blue light, and there has been a need for phosphorescent materials that emit green or blue light and can realize high emission efficiency.

Furthermore, by use of a phosphorescent material that has a broader emission spectrum in the wavelength range of green to blue than a conventional material, a light-emitting element having a higher color rendering index than a conventional element can be realized; for example, in the case where organometallic complexes are used for a lighting device which produces white light with light sources for two colors, it is preferable for a higher color rendering index that the organometallic complex used for one of the light sources have a broader emission spectrum than that used for the other. Moreover, the fabrication of a light-emitting element having a high color rendering index is made possible in addition to that of a light-emitting element which produces white light with light sources for two colors.

Therefore, an object of one embodiment of the present invention is to provide a novel organometallic complex that has a broader emission spectrum in the wavelength range of green to blue. Other objects of embodiments of the present invention are to provide a light-emitting element using the organometallic complex and to provide a light-emitting device, an electronic device, and a lighting device each using the light-emitting element.

One embodiment of the present invention is an organometallic complex in which a 3-(3-pyridyl)-4H-1,2,4-triazole derivative is a ligand and iridium is the central metal. Specific embodiment of the present invention is an organometallic complex represented by a general formula (G1).

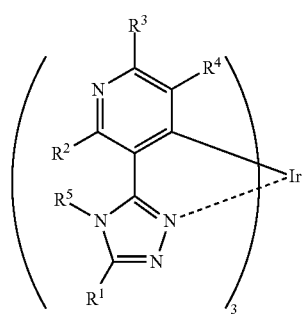

(G1)

In the formula, $R^1$ represents an alkyl group having 1 to 4 carbon atoms, a substituted or unsubstituted haloalkyl group having 1 to 4 carbon atoms, or a substituted or unsubstituted cycloalkyl group having 5 or 6 carbon atoms, $R^2$ to $R^4$ separately represent hydrogen, an alkyl group having 1 to 4 carbon atoms, or a substituted or unsubstituted aryl group having 6 to 13 carbon atoms, and $R^5$ represents an alkyl group having 1 to 4 carbon atoms, a substituted or unsubstituted cycloalkyl group having 5 or 6 carbon atoms, or a substituted or unsubstituted aryl group having 6 to 13 carbon atoms.

It is particularly preferable in the formula that $R^1$ represent an alkyl group having 1 to 4 carbon atoms, or a substituted or unsubstituted cycloalkyl group having 5 or 6 carbon atoms, $R^2$ to $R^4$ separately represent hydrogen, an alkyl group having 1 to 4 carbon atoms, or a substituted or unsubstituted aryl group having 6 to 13 carbon atoms, and $R^5$ represent an alkyl group having 1 to 4 carbon atoms, a substituted or unsubstituted cycloalkyl group having 5 or 6 carbon atoms, or a substituted or unsubstituted aryl group having 6 to 13 carbon atoms.

One embodiment of the present invention is an organometallic complex represented by a general formula (G2).

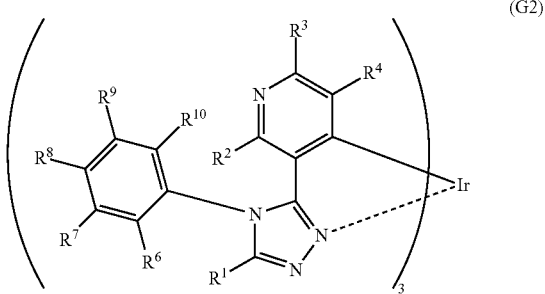

(G2)

In the formula, $R^1$ represents an alkyl group having 1 to 4 carbon atoms, $R^2$ to $R^4$ separately represent hydrogen or an alkyl group having 1 to 4 carbon atoms, and $R^6$ to $R^{10}$ separately represent hydrogen or an alkyl group having 1 to 4 carbon atoms.

In any organometallic complex described above, $R^2$ is preferably a methyl group so that no isomer is produced and the yield of the substance which is the object of the synthesis is improved.

Another embodiment of the present invention is a light-emitting element including, between a pair of electrodes, any organometallic complex described above. In particular, any organometallic complex described above is preferably contained in a light-emitting layer.

A light-emitting device, an electronic device, and a lighting device each using the above light-emitting element also belong to the category of the present invention. Note that the light-emitting device in this specification includes an image display device and a light source. In addition, the light-emitting device includes all the following modules: a module in which a connector, such as a FPC (flexible printed circuit), a TAB (tape automated bonding) tape or a TCP (tape carrier package), is attached to a panel, a module in which a printed wiring board is provided on the tip of a TAB tape or a TCP, and a module in which an IC (integrated circuit) is directly mounted on a light-emitting element by a COG (chip on glass) method.

According to one embodiment of the present invention, a novel organometallic complex that has a broader emission spectrum in the wavelength range of green to blue can be provided. According to other embodiments of the present invention, a light-emitting element using the organometallic complex, and a light-emitting device, an electronic device, and a lighting device each using the light-emitting element can be provided.

BRIEF DESCRIPTION OF THE DRAWINGS

FIG. 8 illustrates lighting devices.

DETAILED DESCRIPTION OF THE INVENTION

Figure 1A:
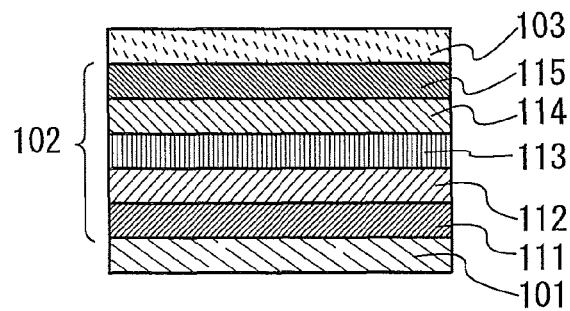
FIGS. 1A to 1C each illustrate a light-emitting element of one embodiment of the present invention.

Embodiments of the present invention will be described with reference to the accompanying drawings. Note that the invention is not limited to the description given below, and it will be easily understood by those skilled in the art that various changes and modifications can be made without departing from the spirit and scope of the invention. Therefore, the invention should not be construed as being limited to the description in the following embodiments. Note also that in the structures described below, the same reference numerals in different drawings represent components that are identical or have similar functions, the description of which is not repeated.

(Embodiment 1)

In Embodiment 1, an organometallic complex of one embodiment of the present invention will be described.

One embodiment of the present invention is an organometallic complex in which a 3-(3-pyridyl)-4H-1,2,4-triazole derivative is a ligand and iridium is the central metal. Specific embodiment of the present invention is an organometallic complex represented by a general formula (G1).

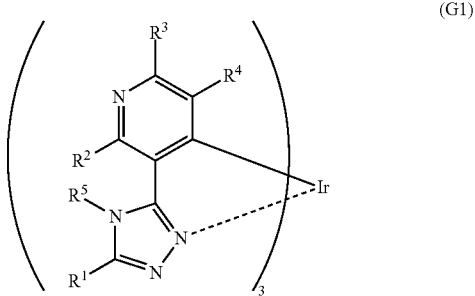

(G1)

In the general formula (G1), $R^1$ represents an alkyl group having 1 to 4 carbon atoms, a substituted or unsubstituted haloalkyl group having 1 to 4 carbon atoms, or a substituted or unsubstituted cycloalkyl group having 5 or 6 carbon atoms, $R^2$ to $R^4$ separately represent hydrogen, an alkyl group having 1 to 4 carbon atoms, or a substituted or unsubstituted aryl group having 6 to 13 carbon atoms, and $R^5$ represents an alkyl group having 1 to 4 carbon atoms, a substituted or unsubstituted cycloalkyl group having 5 or 6 carbon atoms, or a substituted or unsubstituted aryl group having 6 to 13 carbon atoms.

It is particularly preferable in the general formula (G1) that $R^1$ represent an alkyl group having 1 to 4 carbon atoms, or a substituted or unsubstituted cycloalkyl group having 5 or 6 carbon atoms, $R^2$ to $R^4$ separately represent hydrogen, an alkyl group having 1 to 4 carbon atoms, or a substituted or unsubstituted aryl group having 6 to 13 carbon atoms, and $R^5$ represent an alkyl group having 1 to 4 carbon atoms, a substituted or unsubstituted cycloalkyl group having 5 or 6 carbon atoms, or a substituted or unsubstituted aryl group having 6 to 13 carbon atoms.

One embodiment of the present invention is an organometallic complex represented by a general formula (G2).

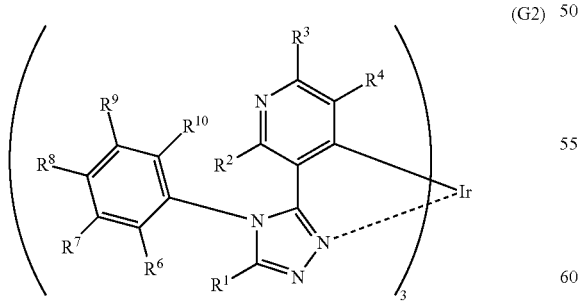

(G2)

In the general formula (G2), $R^1$ represents an alkyl group having 1 to 4 carbon atoms, $R^2$ to $R^4$ separately represent hydrogen or an alkyl group having 1 to 4 carbon atoms, and $R^6$ to $R^{10}$ separately represent hydrogen or an alkyl group having 1 to 4 carbon atoms.

In any organometallic complex described above, $R^2$ is preferably a methyl group so that no isomer is produced and the yield of the substance which is the object of the synthesis is improved.

[Method of Synthesizing Organometallic Complex Represented by General Formula (G1)]

An example of a method of synthesizing an organometallic complex represented by the following general formula (G1) is described.

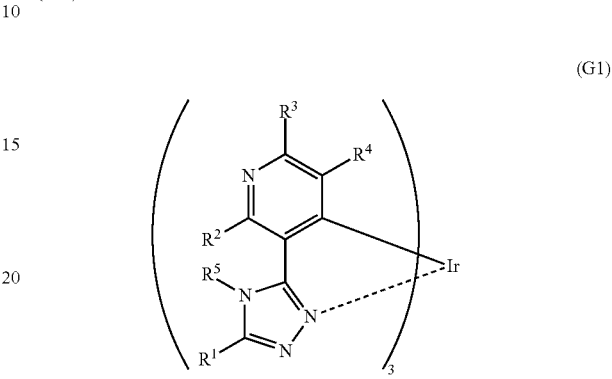

(G1)

In the general formula (G1), $R^1$ represents an alkyl group having 1 to 4 carbon atoms, a substituted or unsubstituted haloalkyl group having 1 to 4 carbon atoms, or a substituted or unsubstituted cycloalkyl group having 5 or 6 carbon atoms, $R^2$ to $R^4$ separately represent hydrogen, an alkyl group having 1 to 4 carbon atoms, or a substituted or unsubstituted aryl group having 6 to 13 carbon atoms, and $R^5$ represents an alkyl group having 1 to 4 carbon atoms, a substituted or unsubstituted cycloalkyl group having 5 or 6 carbon atoms, or a substituted or unsubstituted aryl group having 6 to 13 carbon atoms.

Step 1: Method of Synthesizing 3-(3-Pyridyl)-4H-1,2,4-triazole Derivative

First, a method of synthesizing a 3-(3-pyridyl)-4H-1,2,4-triazole derivative represented by the following general formula (G0) is described since it is a novel substance.

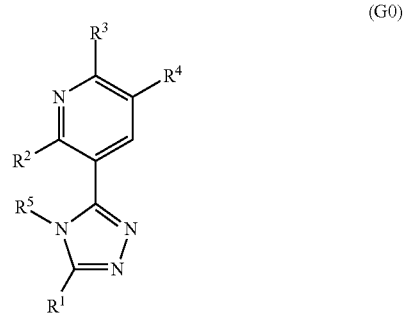

(G0)

In the general formula (G0), $R^1$ represents an alkyl group having 1 to 4 carbon atoms, a substituted or unsubstituted haloalkyl group having 1 to 4 carbon atoms, or a substituted or unsubstituted cycloalkyl group having 5 or 6 carbon atoms, $R^2$ to $R^4$ separately represent hydrogen, an alkyl group having 1 to 4 carbon atoms, or a substituted or unsubstituted aryl group having 6 to 13 carbon atoms, and $R^5$ represents an alkyl group having 1 to 4 carbon atoms, a substituted or unsubstituted cycloalkyl group having 5 or 6 carbon atoms, or a substituted or unsubstituted aryl group having 6 to 13 carbon atoms.

Note that specific examples of an alkyl group having 1 to 4 carbon atoms in $R^1$ and $R^5$ are a methyl group, an ethyl group, a propyl group, an isopropyl group, a butyl group, a sec-butyl group, an isobutyl group, and a tert-butyl group. In addition, specific examples of the substituted or unsubstituted haloalkyl group having 1 to 4 carbon atoms in $R^1$ are a fluoromethyl group, a difluoromethyl group, a trifluoromethyl group, a chloromethyl group, a dichloromethyl group, a bromomethyl group, a 1,1-difluoroethyl group, a 2,2,2-trifluoroethyl group, a 3,3,3-trifluoropropyl group, and a 1,1,1,3,3,3-hexafluoroisopropyl group. Further, specific examples of the substituted or unsubstituted cycloalkyl group having 5 or 6 carbon atoms in $R^1$ and $R^5$ are a cyclopentyl group, a cyclohexyl group, a 1-methylcyclohexyl group, and a 2,6-dimethylcyclohexyl group.

Specific examples of $R^2$ to $R^4$ are a methyl group, an ethyl group, a propyl group, an isopropyl group, a tert-butyl group, a hexyl group, a cyclohexyl group, a substituted phenyl group with one or more methyl groups, a phenyl group, a biphenyl group, a substituted phenyl group with one or more methyl groups, a substituted phenyl group with one or more ethyl groups, a substituted phenyl group with one or more isopropyl groups, a substituted phenyl group with a tert-butyl group, a substituted phenyl group with a fluoro group, and a substituted phenyl group with a trifluoromethyl group.

As illustrated in a scheme (a) below, a pyridine-3-hydrazide compound (A1) is reacted with a thioether compound having $R^1$ and $R^5$ or an N-substituted thioamide compound having $R^1$ and $R^5$ (A2), so that a 3-(3-pyridyl)-4H-1,2,4-triazole derivative can be obtained.

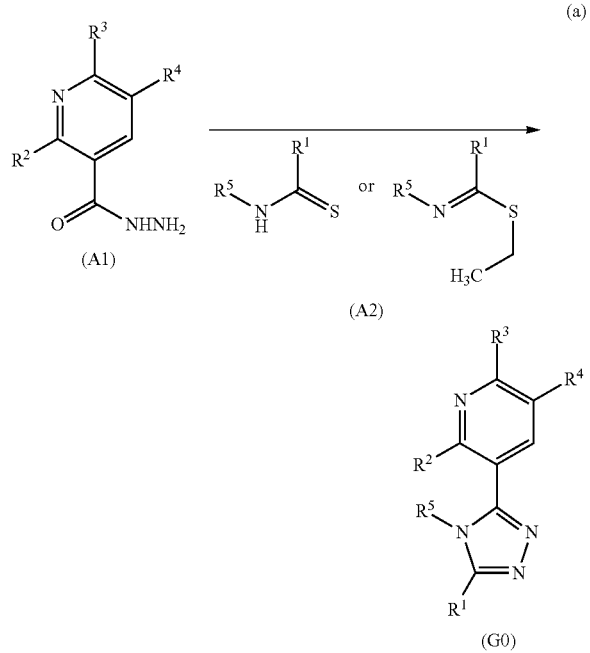

(a)

In the scheme (a), $R^1$ represents an alkyl group having 1 to 4 carbon atoms, a substituted or unsubstituted haloalkyl group having 1 to 4 carbon atoms, or a substituted or unsubstituted cycloalkyl group having 5 or 6 carbon atoms, $R^2$ to $R^4$ separately represent hydrogen, an alkyl group having 1 to 4 carbon atoms, or a substituted or unsubstituted aryl group having 6 to 13 carbon atoms, and $R^5$ represents an alkyl group having 1 to 4 carbon atoms, a substituted or unsubstituted cycloalkyl group having 5 or 6 carbon atoms, or a substituted or unsubstituted aryl group having 6 to 13 carbon atoms.

Note that the method of synthesizing a 3-(3-pyridyl)-4H-1,2,4-triazole derivative is not limited to the scheme (a). For example, there is a method in which a thioether compound having 3-pyridyl and $R^5$ or an N-substituted thioamide compound having 3-pyridyl and $R^5$ is reacted with a hydrazide compound having $R^1$.

As illustrated in a scheme (a') below, there is also a method in which a dihydrazide compound (A1') and a primary amine compound (A2') are reacted.

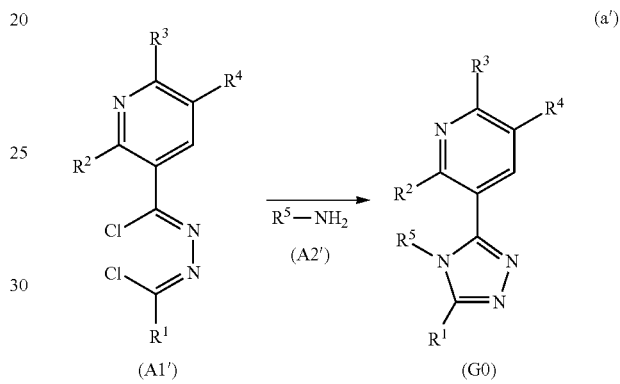

(a')

In the scheme (a'), $R^1$ represents an alkyl group having 1 to 4 carbon atoms, a substituted or unsubstituted haloalkyl group having 1 to 4 carbon atoms, or a substituted or unsubstituted cycloalkyl group having 5 or 6 carbon atoms, $R^2$ to $R^4$ separately represent hydrogen, an alkyl group having 1 to 4 carbon atoms, or a substituted or unsubstituted aryl group having 6 to 13 carbon atoms, and $R^5$ represents an alkyl group having 1 to 4 carbon atoms, a substituted or unsubstituted cycloalkyl group having 5 or 6 carbon atoms, or a substituted or unsubstituted aryl group having 6 to 13 carbon atoms.

As described above, the 3-(3-pyridyl)-4H-1,2,4-triazole derivative represented by the general formula (G0) can be synthesized by a simple synthesis scheme.

Step 2: Method of Synthesizing Ortho-Metalated Complex Having 3-(3-Pyridyl)-4H-1,2,4-triazole Derivative as Ligand As shown in a synthesis scheme (b) below, the 3-(3-pyridyl)-4H-1,2,4-triazole derivative (G0), which is obtained in Step 1, and an iridium metal compound including halogen (e.g., iridium chloride hydrate or ammonium hexachloroiridate) or an iridium organometallic complex (e.g., an acetylacetonate complex, a diethyl sulfide complex, a μ-halogen bridging binuclear complex having a 3-(3-pyridyl)-4H-1,2,4-triazole derivative as a ligand, or a μ-oxo bridging binuclear complex having a 3-(3-pyridyl)-4H-1,2,4-triazole derivative as a ligand) are mixed and then heated, so that the organometallic complex represented by the general formula (G1) can be obtained.

There is no particular limitation on a heating means, and an oil bath, a sand bath, or an aluminum block may be used as the heating means. Further, microwaves can be used as the heating means. This heating process may be performed after the 3-(3-pyridyl)-4H-1,2,4-triazole derivative (G0), which is obtained in Step 1, and an iridium metal compound including halogen or an iridium organometallic complex compound are dissolved in an alcohol-based solvent (e.g., glycerol, ethylene glycol, 2-metoxyethanol, or 2-ethoxyethanol).

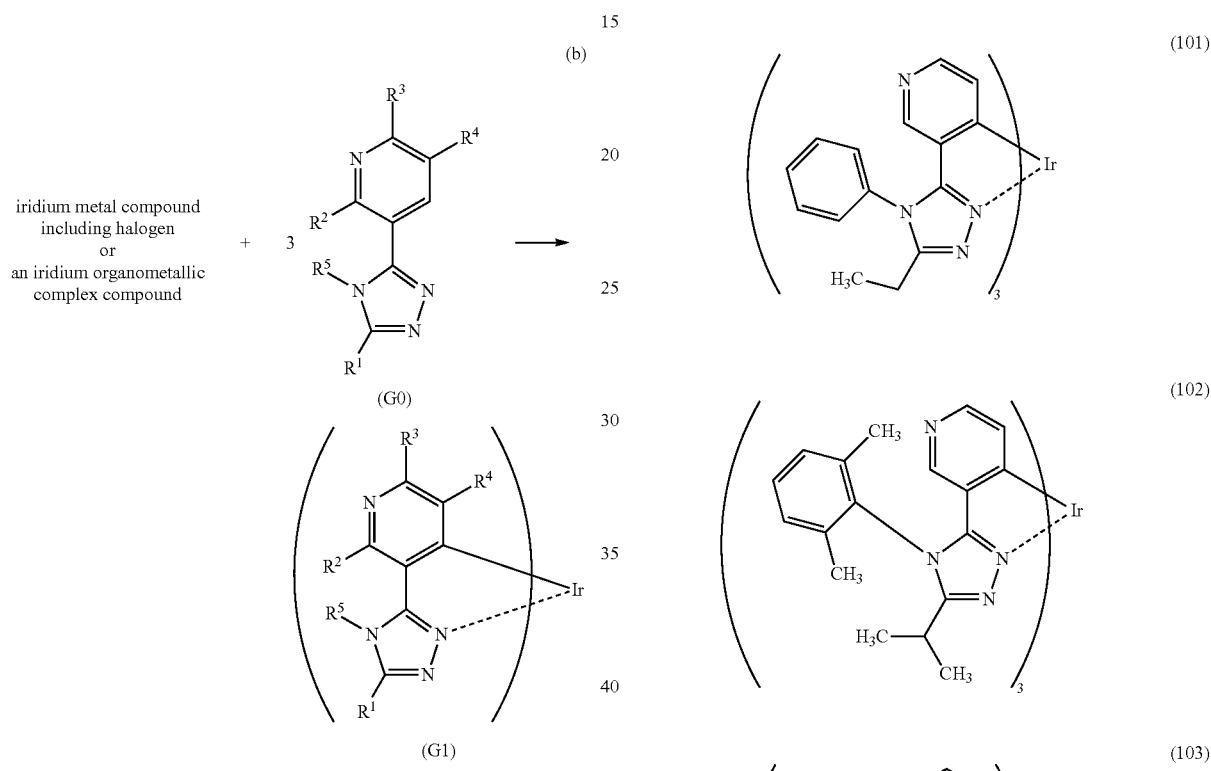

Since the above-described compounds (A1), (A2), (A1'), and (A2') are commercially available as a wide variety of compounds or synthesis thereof is feasible, a great variety of derivatives can be synthesized as the 3-(3-pyridyl)-4H-1,2,4-triazole derivative represented by the general formula (G0). Thus, abundant variations in ligands feature an organometallic complex of one embodiment of the present invention represented by the general formula (G1). Moreover, in fabrication of a light-emitting element, fine adjustment of element characteristics required for the light-emitting element can be performed easily by using an organometallic complex having such abundant variations in ligands.

Although examples of the synthesis methods are described above, an organometallic complex which is a disclosed embodiment of the present invention may be synthesized by any other synthesis method.

Specific structural formulae of an organometallic complex of one embodiment of the present invention will be illustrated in the following structural formulae (100) to (135); however, the present invention is not limited thereto.

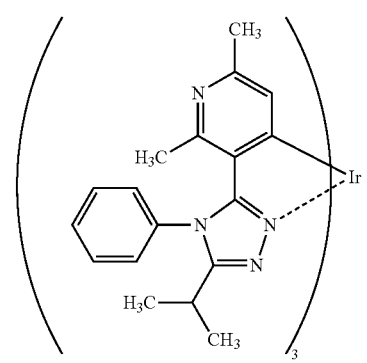 (105)
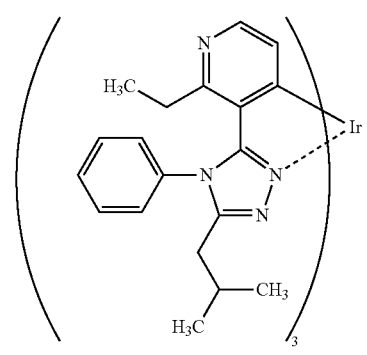 (106)
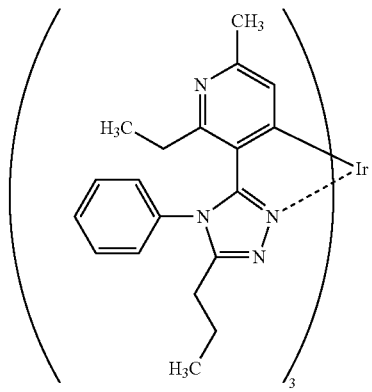 (107)
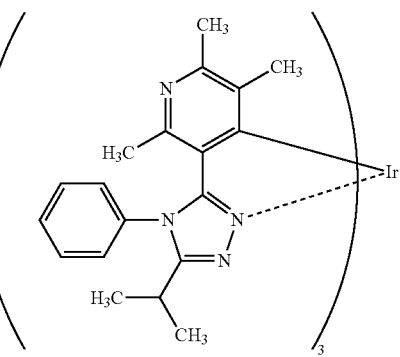 (108)
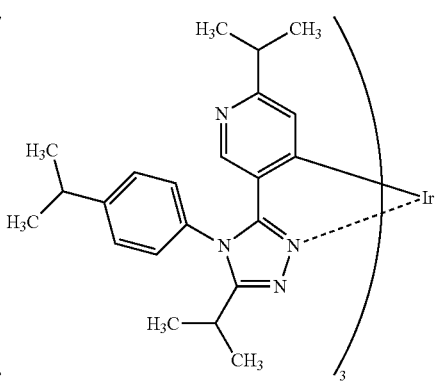 (109)
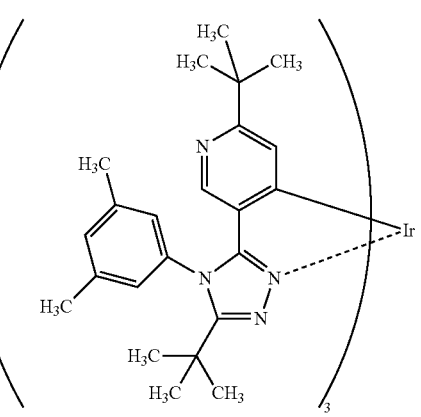 (120)
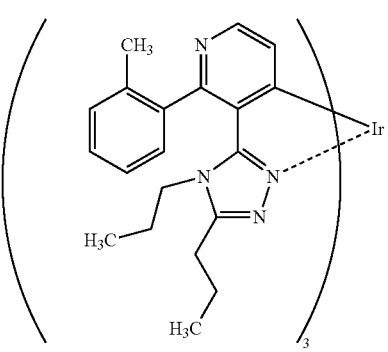 (121)
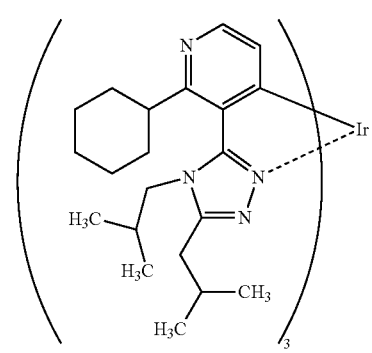 (122)

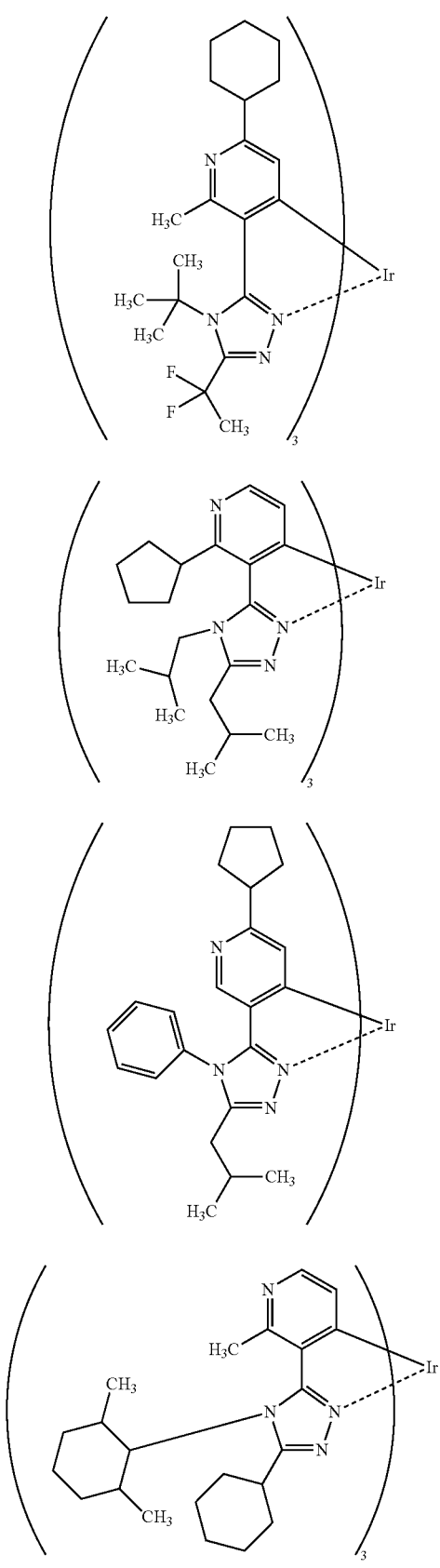
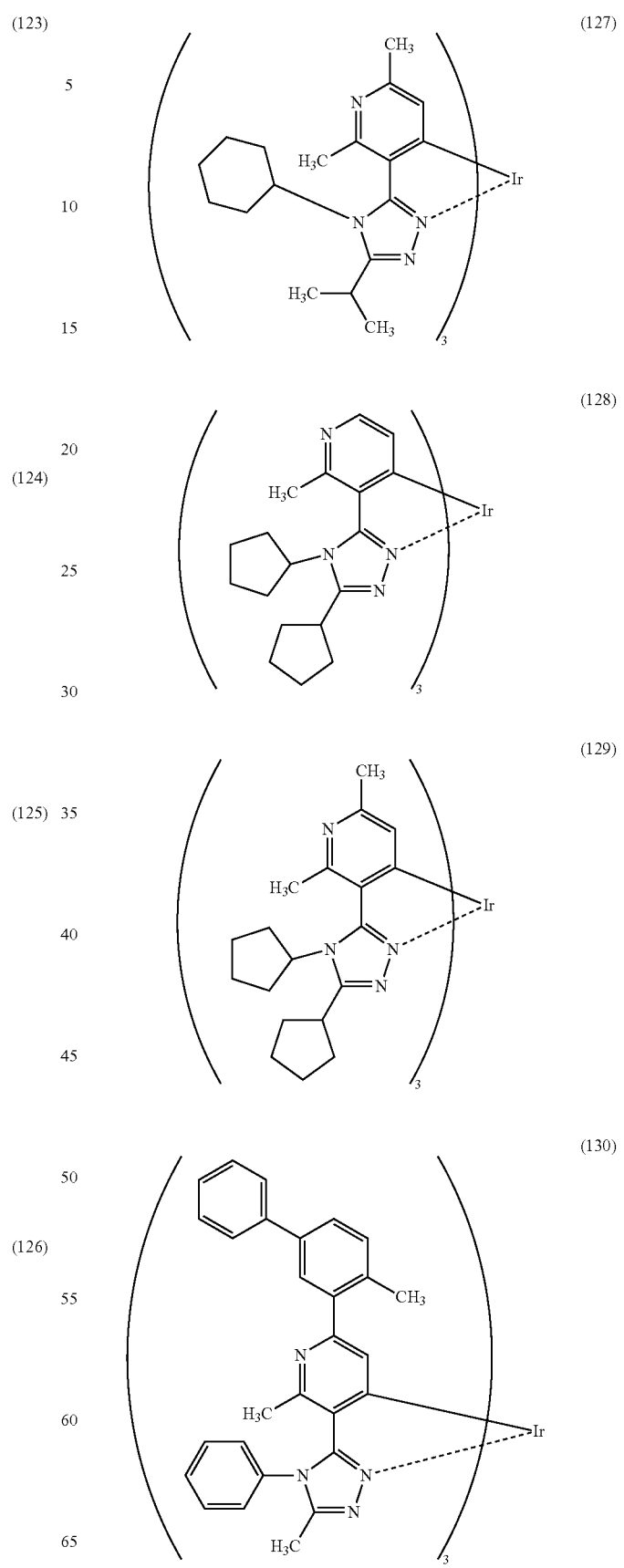

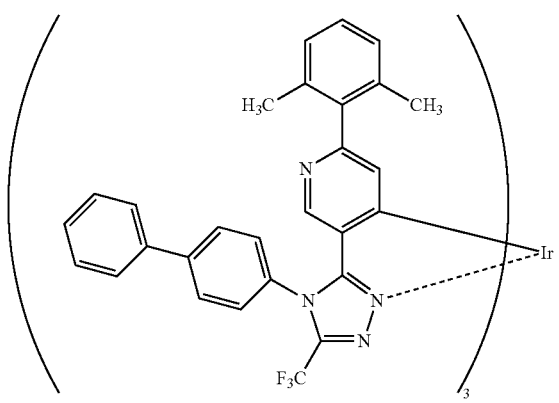

(131)

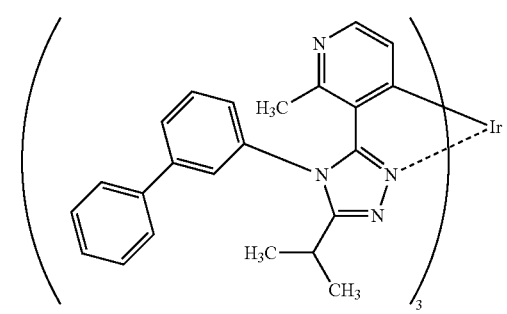

(132)

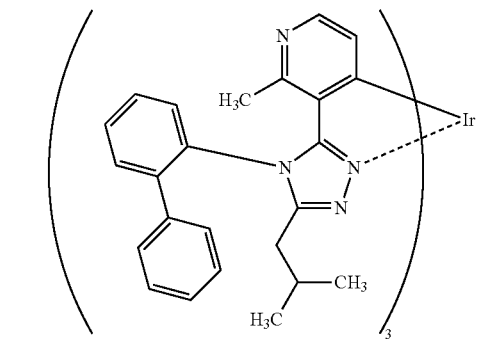

(133)

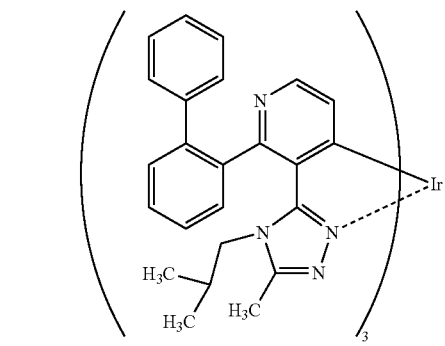

(134)

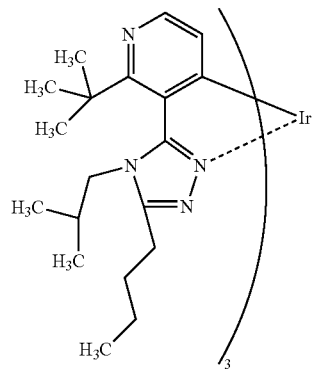

(135)

Depending on the type of the ligand, there can be stereoisomers of the organometallic complexes represented by the above structural formulae (100) to (135), and such isomers are included in the category of an organometallic complex of one embodiment of the present invention.

Any organometallic complex of one embodiment of the present invention which is described above can be used as a light-emitting material or a light-emitting substance of a light-emitting element since the organometallic complex has a broader emission spectrum in the wavelength range of green to blue.

(Embodiment 2)

In Embodiment 2, as one embodiment of the present invention, a light-emitting element in which an organometallic complex described in Embodiment 1 is used for a light-emitting layer will be described with reference to FIG. 1A.

FIG. 1A illustrates a light-emitting element having an EL layer 102 between a first electrode 101 and a second electrode 103. The EL layer 102 includes a light-emitting layer 113. The light-emitting layer 113 includes an organometallic complex of one embodiment of the present invention which is described in Embodiment 1.

By application of a voltage to such a light-emitting element, holes injected from the first electrode 101 side and electrons injected from the second electrode 103 side recombine in the light-emitting layer 113 to raise the organometallic complex to an excited state. Then, light is emitted when the organometallic complex in the excited state returns to the ground state. Thus, the organometallic complex of one embodiment of the present invention functions as a light-emitting substance in the light-emitting element. Note that in the light-emitting element described in this embodiment, the first electrode 101 functions as an anode and the second electrode 103 functions as a cathode.

For the first electrode 101 functioning as an anode, any of metals, alloys, electrically conductive compounds, mixtures thereof, and the like which has a high work function (specifically, a work function of 4.0 eV or more) is preferably used. Specific examples are indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide, and the like. Other than these, gold, platinum, nickel, tungsten, chromium, molybdenum, iron, cobalt, copper, palladium, titanium, or the like can be used.

When a layer included in the EL layer 102 which is formed in contact with the first electrode 101 is formed using a later described composite material formed by combining an organic compound and an electron acceptor (acceptor), as a substance used for the first electrode 101, any of a variety of metals, alloys, and electrically-conductive compounds, a mixture thereof, and the like can be used regardless of the work function; for example, aluminum, silver, an alloy containing aluminum (e.g., Al—Si), or the like can also be used.

The first electrode 101 can be formed by, for example, a sputtering method, an evaporation method (including a vacuum evaporation method), or the like.

The EL layer 102 formed over the first electrode 101 has at least the light-emitting layer 113 and is formed to include an organometallic complex of one embodiment of the present invention. For part of the EL layer 102, a known substance can be used, and either a low molecular compound or a high molecular compound can be used. Note that substances forming the EL layer 102 may consist of organic compounds or may include an inorganic compound as a part.

As illustrated in FIG. 1A, the EL layer 102 is formed by stacking as appropriate the hole-injection layer 111 containing a substance having a high hole-injection property, the hole-transport layer 112 containing a substance having a high hole-transport property, the electron-transport layer 114 containing a substance having a high electron-transport property, the electron-injection layer 115 containing a substance having a high electron-injection property, and the like in combination in addition to the light-emitting layer 113.

The hole-injection layer 111 is a layer containing a substance having a high hole-injection property. Examples of a substance having a high hole-injection property which can be used are metal oxides, such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. Other examples of a substance that can be used are phthalocyanine-based compounds, such as phthalocyanine (abbreviation: $H_2Pc$) and copper(II) phthalocyanine (abbreviation: CuPc).

Other examples of a substance that can be used are aromatic amine compounds which are low molecular organic compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Still other examples of a substance that can be used are high molecular compounds (e.g., oligomers, dendrimers, and polymers), such as poly(N-vinylcarbazole) (abbreviation: PVK), poly(-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD), and high molecular compounds to which acid is added, such as poly(3,4-ethylenedioxythiophene)/poly(styrenesulfonic acid) (PEDOT/PSS), or polyaniline/poly(styrenesulfonic acid) (PAni/PSS).

For the hole-injection layer 111, the composite material formed by combining an organic compound and an electron acceptor (acceptor) may be used. Such a composite material, in which holes are generated in the organic compound by the electron acceptor, has an excellent hole injection and transport properties. In this case, the organic compound is preferably a material excellent in transporting the generated holes (a substance having a high hole-transport property).

Examples of the organic compound used for the composite material are a variety of compounds, such as aromatic amine compounds, carbazole derivatives, aromatic hydrocarbons, and high molecular compounds (e.g., oligomers, dendrimers, and polymers). The organic compound used for the composite material is preferably organic compounds having a high hole-transport property, and specifically preferably a substance having a hole mobility of $10^{-6}$ cm$^2$/Vs or more. Note that other than these substances, any substance that has a property of transporting more holes than electrons may be used. Organic compounds that can be used for the composite material will be specifically described below.

Examples of an organic compound that can be used for the composite material are aromatic amine compounds, such as TDATA, MTDATA, DPAB, DNTPD, DPA3B, PCzPCA1, PCzPCA2, PCzPCN1,4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives, such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Other examples of an organic compound that can be used are aromatic hydrocarbon compounds, such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Other examples of an organic compound that can be used are aromatic hydrocarbon compounds, such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Further, examples of the electron acceptor are organic compounds, such as 7,7,8,8-tetracyano-2,3,5,6-tetrafluoroquinodimethane (abbreviation: $F_4$-TCNQ) and chloranil, transition metal oxides, and oxides of metals that belong to Groups 4 to 8 in the periodic table. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air and its hygroscopic property is low and is easily treated.

The composite material may be formed using the above-described electron acceptor and the above-described high molecular compound, such as PVK, PVTPA, PTPDMA, or Poly-TPD, and used for the hole-injection layer 111.

The hole-transport layer 112 is a layer that contains a substance having a high hole-transport property. As the substance having a high hole-transport property, the following aromatic amine compounds can be given: NPB, TPD, BPAFLP, 4,4'-bis[N-(9,9-dimethylfluoren-2-yl)-N-phenylamino]biphenyl (abbreviation: DFLDPBi), 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than the above substances, any substance that has a property of transporting more holes than electrons may be used. Further, the layer including a substance having a high hole-transport property is not limited to a single layer, and may be a stack of two or more layers containing any of the above substances.

For the hole-transport layer 112, a carbazole derivative, such as CBP, CzPA, or PCzPA, or an anthracene derivative, such as t-BuDNA, DNA, or DPAnth, may be used.

For the hole-transport layer 112, a high molecular compound, such as PVK, PVTPA, PTPDMA, or Poly-TPD, can be used.

The light-emitting layer 113 is a layer that contains an organometallic complex which is one embodiment of the present invention. The light-emitting layer 113 may be formed with a thin film containing an organometallic complex of one embodiment of the present invention. The light-emitting layer 113 may be a thin film in which the organometallic complex which is one embodiment of the present invention is dispersed as a guest in a substance as a host which has higher triplet excitation energy than the organometallic complex of one embodiment of the present invention; thus, quenching of light emission from the organometallic complex caused depending on the concentration can be prevented. Note that the triplet excitation energy indicates an energy gap between a ground state and a triplet excited state.

The electron-transport layer 114 is a layer including a substance having a high electron-transport property. As the substance having a high electron-transport property, the following metal complexes can be given: Alq$_3$; tris(4-methyl-8-quinolinolato)aluminum (abbreviation: Almq$_3$); bis(10-hydroxybenzo[h]-quinolinato)beryllium (abbreviation: BeBq$_2$); BAlq; Zn(BOX)$_2$; and bis[2-(2-hydroxyphenyl)benzothiazolato]zinc (abbreviation: Zn(BTZ)$_2$). Other examples of the substance that can be used are heteroaromatic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazol-2-yl)stilbene (abbreviation: BzOs), and high molecular compounds, such as poly (2,5-pyridinediyl) (abbreviation: PPy), poly[(9,9-dihexylfluorene-2,7-diyl)-co-(pyridine-3,5-diyl)] (abbreviation: PF-Py) and poly[(9,9-dioctylfluorene-2,7-diyl)-co-(2,2'-bipyridine-6,6'-diyl)] (abbreviation: PF-BPy). The substances described here are mainly substances having an electron mobility of $10^{-6}$ cm$^2$/Vs or more. Note that other than the above substances, any substance that has a property of transporting more electrons than holes may be used for the electron-transport layer.

Further, the electron-transport layer is not limited to a single layer, and may be a stack of two or more layers containing any of the above substances are stacked.

The electron-injection layer 115 is a layer that contains a substance having a high electron-injection property. Examples of the substance that can be used for the electron-injection layer 115 are alkali metals, alkaline earth metals, and compounds thereof, such as lithium, cesium, calcium, lithium fluoride, cesium fluoride, calcium fluoride, and lithium oxide, rare earth-metal compounds, such as erbium fluoride, and the above-mentioned substances for forming the electron-transport layer 114.

Alternatively, a composite material formed by combining an organic compound and an electron donor (donor) may be used for the electron-injection layer 115. Such a composite material, in which electrons are generated in the organic compound by the electron donor, has excellent electron injection and transport properties. The organic compound here is preferably a material excellent in transporting the generated electrons, as which specifically any of the above substances (such as metal complexes and heteroaromatic compounds) for the electron-transport layer 114 can be used. The electron donor can be a substance exhibiting an electron-donating property for the organic compound. Specific examples of the electron donor are alkali metals, alkaline earth metals, and rare earth-metals, such as lithium, cesium, magnesium, calcium, erbium, and ytterbium. Any of alkali metal oxides and alkaline earth metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 111, the hole-transport layer 112, the light-emitting layer 113, the electron-transport layer 114, and the electron-injection layer 115 which are described above can each be formed by a method, such as an evaporation method (e.g., a vacuum evaporation method), an inkjet method, or a coating method.

For the second electrode 103 functioning as a cathode, any of metals, alloys, electrically conductive compounds, mixtures thereof, and the like which has a low work function (specifically, a work function of 3.8 eV or less) is preferably used. Specific examples of the substance that can be used are elements that belong to Groups 1 and 2 in the periodic table, that is, alkali metals such as lithium and cesium, alkaline earth metals such as magnesium, calcium, and strontium, alloys thereof (e.g., Mg—Ag and Al—Li), rare earth-metals such as europium and ytterbium, alloys thereof, aluminum, silver, and the like.

When a layer included in the EL layer 102 which is formed in contact with the second electrode 103 is formed using the composite material formed by combining the organic compound and the electron donor (donor), which are described above, a variety of conductive materials such as Al, Ag, ITO, and indium oxide-tin oxide containing silicon or silicon oxide can be used regardless of the work function.

Note that when the second electrode 103 is formed, a vacuum evaporation method or a sputtering method can be used. In the case of using a silver paste or the like, a coating method, an inkjet method, or the like can be used.

In the above-described light-emitting element, a current flows due to a potential difference generated between the first electrode 101 and the second electrode 103 and holes and electrons recombine in the EL layer 102, so that light is emitted. Then, this light emission is extracted outside through one or both of the first electrode 101 and the second electrode 103. Therefore, one or both of the first electrode 101 and the second electrode 103 are electrodes having a property of transmitting visible light.

Note that by use of the light-emitting element described in this embodiment, a passive matrix light-emitting device or an active matrix light-emitting device in which driving of the light-emitting element is controlled by a thin film transistor (TFT) can be manufactured.

In the case where an active matrix light-emitting device is manufactured, there is no particular limitation on the structure of the TFT: for example, a staggered TFT or an inverted staggered TFT can be used as appropriate; and a driver circuit formed in a TFT substrate may be formed with an n-type TFT and a p-type TFT, or with either an n-type TFT or a p-type TFT. In addition, there is no particular limitation on the crystallinity of a semiconductor film used for the TFT, and an amorphous semiconductor film or a crystalline semiconductor film may be used, for example. As a material of the semiconductor film, a compound semiconductor such as GaAs, InP, SiC, ZnSe, GaN, or SiGe can be used as well as an element such as silicon or germanium. An oxide semiconductor such as zinc oxide, tin oxide, magnesium zinc oxide, gallium oxide, or indium oxide, an oxide semiconductor including two or more of the above oxide semiconductors, or the like can be used.

Note that, in Embodiment 2, an organometallic complex of one embodiment of the present invention, which is used for the light-emitting layer 113, has a broader emission spectrum in the wavelength range of green to blue. Thus, a light-emitting element having a high color rendering index can be realized.

Note that in Embodiment 2, any of the structures described in Embodiment 1 can be used in appropriate combination.

(Embodiment 3)

The light-emitting element which is one embodiment of the present invention may have a plurality of light-emitting layers. A plurality of light-emitting layers is provided so that each light-emitting layer emits light, so that a mixture of the light can be obtained. Thus, for example, emission of white light can be obtained. In Embodiment 3, a mode of a light-emitting element having a plurality of light-emitting layers will be described with reference to FIG. 1B.

Figure 1B:
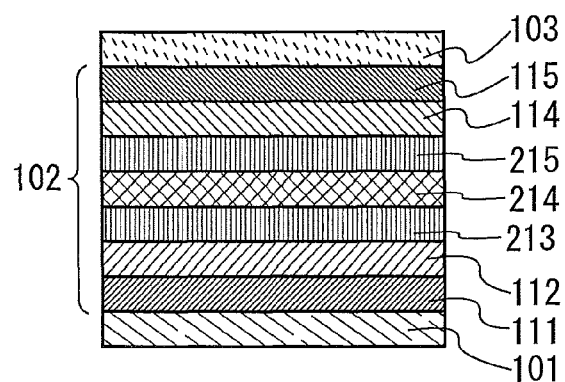

FIG. 1B illustrates a light-emitting element having the EL layer 102 between the first electrode 101 and the second electrode 103. The EL layer 102 includes a first light-emitting layer 213 and a second light-emitting layer 215, so that light emission that is a mixture of light emission from the first light-emitting layer 213 and light emission from the second light-emitting layer 215 can be obtained in the light-emitting element illustrated in FIG. 1B. A separation layer 214 is preferably formed between the first light-emitting layer 213 and the second light-emitting layer 215.

Embodiment 3 gives descriptions of a light-emitting element that emits white light, in which the first light-emitting layer 213 contains an organometallic complex of one embodiment of the present invention and the second light-emitting layer 215 contains an organic compound whose emission exhibits yellow to red, but the present invention is not limited thereto.

While an organometallic complex which is one embodiment of the present invention is used for the second light-emitting layer 215, another light-emitting substance may be applied to the first light-emitting layer 213.

The EL layer 102 may have three or more light-emitting layers.

When a voltage is applied so that the potential of the first electrode 101 is higher than the potential of the second electrode 103, a current flows between the first electrode 101 and the second electrode 103, and holes and electrons recombine in the first light-emitting layer 213, the second light-emitting layer 215, or the separation layer 214. Generated excitation energy is distributed to both the first light-emitting layer 213 and the second light-emitting layer 215 to raise each of a first light-emitting substance included in the first light-emitting layer 213 and a second light-emitting substance included in the second light-emitting layer 215 to an excited state. The first and second light-emitting substances each in the excited state emit light while returning to the ground state.

The first light-emitting layer 213 contains an organometallic complex which is one embodiment of the present invention, and blue light emission can be obtained. The first light-emitting layer 213 can have the same structure as the light-emitting layer 113 described in Embodiment 2.

The second light-emitting layer 215 contains a light-emitting substance typified by the following compounds: fluorescent compounds, such as 2-(2-{2-[4-(dimethylamino) phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis (4-methylphenyl)acenaphtho[1,2-a]fluoranthene-3,10-diamine (abbreviation: p-mPhAFD), 2-{2-isopropyl-6-[2-(1, 1,7,7-tetramethyl-2,3,6,7-tetrahydro-1H,5H-benzo[ij] quinolizin-9-yl)ethenyl]-4H-pyran-4-ylidene}propanedinitrile (abbreviation: DCJTB), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis {2-[4-(dimethylamino)phenyl]ethenyl}-4H-pyran-4-ylidene)propanedinitrile (abbreviation: BisDCM), and 2-{2, 6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM); and phosphorescent compounds, such as bis[2-(2'-benzo[4,5-a] thienyl)pyridinato-N,$C^{3'}$]iridium(III)acetylacetonate (abbreviation: Ir(btp)$_2$(acac)), bis(1-phenylisoquinolinato-N,$C^{2'}$) iridium(III)acetylacetonate (abbreviation: Ir(piq)$_2$(acac)), (acetylacetonato)bis[2,3-bis(4-fluorophenyl)quinoxalinato] iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H, 23H-porphyrinplatinum(II) (abbreviation: PtOEP), tris(1,3-diphenyl-1,3-propanedionato)(monophenanthroline) europium(III) (abbreviation: Eu(DBM)$_3$(Phen)), and tris[1-(2-thenoyl)-3,3,3-trifluoroacetonato](monophenanthroline) europium(III) (abbreviation: Eu(TTA)$_3$(Phen)), from which light emission having an emission peak at 560 nm to 700 nm (i.e. light emission from yellow to red) is obtained.

In addition, when the second light-emitting substance is a fluorescent compound, the second light-emitting layer 215 preferably has a structure in which the second light-emitting substance is dispersed as a guest in a substance as a first host which has higher singlet excitation energy than the second light-emitting substance. When the second light-emitting substance is a phosphorescent compound, the second light-emitting layer 215 preferably has a structure in which the second light-emitting substance is dispersed as a guest in a substance as a host material which has higher triplet excitation energy than the second light-emitting substance. As the host material, DNA, t-BuDNA, or the like can be used other than NPB, CBP, TCTA, and the like described above. Note that the singlet excitation energy is an energy difference between a ground state and a singlet excited state. In addition, the triplet excitation energy is an energy difference between a ground state and a triplet excited state.

Specifically, the separation layer 214 can be formed using TPAQn, NPB, CBP, TCTA, Znpp$_2$, ZnBOX or the like described above. By thus providing the separation layer 214, it is possible to prevent a defect in which only one of the first light-emitting layer 213 and the second light-emitting layer 215 has an excessively high emission intensity. Note that although not necessarily needed, the separation layer 214 may be provided as appropriate to adjust the ratio in emission intensity of the first light-emitting layer 213 to the second light-emitting layer 215.

Other than the light-emitting layers, the hole-injection layer 111, the hole-transport layer 112, the electron-transport layer 114, and the electron-injection layer 115 are provided in the EL layer 102; as for structures of these layers, the structures of the respective layers described in Embodiment 2 can be applied. However, these layers are not necessarily needed and may be provided as appropriate according to element characteristics.

Note that the structure described in this embodiment can be combined with any of the structures described in Embodiments 1 and 2 as appropriate.

(Embodiment 4)

Figure 1C:
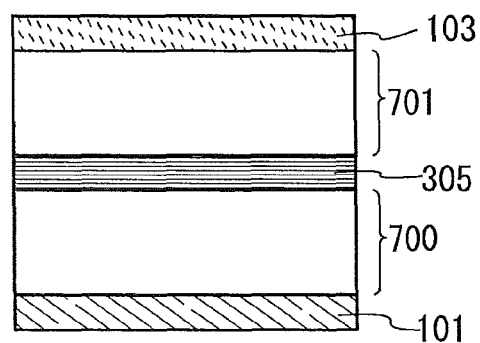

In Embodiment 4, as one embodiment of the present invention, a structure of a light-emitting element which includes a plurality of EL layers (hereinafter, referred to as a stacked-type element) will be described with reference to FIG. 1C. This light-emitting element is a stacked-type light-emitting element having a plurality of EL layers (a first EL layer 700 and a second EL layer 701) between a first electrode 101 and a second electrode 103. Note that the number of the EL layers is two in this embodiment but may be three or more.

In Embodiment 3, the structures described in Embodiment 2 can be applied to the first electrode 101 and the second electrode 103.

In Embodiment 3, all or any of the plurality of EL layers (the first EL layer 700 and the second EL layer 701) may have the same structure as the EL layer described in Embodiment 2. In other words, the structures of the first EL layer 700 and the second EL layer 701 may be the same as or different from each other and can be the same as in Embodiment 2.

Further, a charge generation layer 305 is provided between the plurality of EL layers (the first EL layer 700 and the second EL layer 701). The charge generation layer 305 has a function of injecting electrons into one of the EL layers and injecting holes into the other of the EL layers when a voltage is applied to the first electrode 101 and the second electrode 103. In the case of this embodiment, when a voltage is applied so that the potential of the first electrode 101 is higher than that of the second electrode 103, the charge generation layer 305 injects electrons into the first EL layer 700 and injects holes into the second EL layer 701.

Note that the charge generation layer 305 preferably has a property of transmitting visible light in terms of light extraction efficiency. Further, the charge generation layer 305 functions even if it has lower conductivity than the first electrode 101 or the second electrode 103.

The charge generation layer 305 may have a structure in which it includes the organic compound having a high hole-transport property and the electron acceptor (acceptor) or a structure in which it includes an organic compound having a high electron-transport property and the electron donor (donor), or may be a stack of both of these structures.

In the case of the structure in which the electron acceptor is added to the organic compound having a high hole-transport property, examples of the substance that can be used as the organic compound having a high hole-transport property are aromatic amine compounds, such as NPB, TPD, TDATA, MTDATA, and 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than the above substances, any organic compound that has a property of transporting more holes than electrons may be used.

Examples of the electron acceptor are 7,7,8,8-tetracyano-2,3,5,6-tetrafluoroquinodimethane (abbreviation: F$_4$-TCNQ), chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because of their high electron-acceptor properties. Among these, molybdenum oxide is especially preferable since it is stable in the air and its hygroscopic property is low and is easily treated.

In the case of the structure in which the electron donor is added to the organic compound having a high electron-transport property, any of the following substances can be used as the organic compound having a high electron-transport property which can be used, for example: metal complexes having a quinoline skeleton or a benzoquinoline skeleton such as Alq, Almq$_3$, BeBq$_2$, and BAlq; metal complexes having an oxazole-based ligand or a thiazole-based ligand, such as Zn(BOX)$_2$ and Zn(BTZ)$_2$; and the like. Examples other than the metal complexes are PBD, OXD-7, TAZ, BPhen, BCP, and the like. The substances described here are mainly substances having an electron mobility of $10^{-6}$ cm$^2$/Vs or more. Note that other than the above substances, any organic compound that has a property of transporting more electrons than holes may be used.

Examples of the electron donor that can be used are alkali metals, alkaline-earth metals, rare-earth metals, metals that belong to Group 13 in the periodic table and oxides or carbonates thereof, and preferably specifically lithium, cesium, magnesium, calcium, ytterbium, indium, lithium oxide, cesium carbonate, and the like. An organic compound such as tetrathianaphthacene may be used as the electron donor.

Note that by forming the charge generation layer 305 with any of the above materials, it is possible to suppress an increase in drive voltage caused when the EL layers are stacked.

Although the light-emitting element having two EL layers is described in this embodiment, the embodiment can be similarly applied to a light-emitting element in which three or more EL layers are stacked. When a plurality of EL layers with a charge generation layer interposed therebetween is arranged between a pair of electrodes, as in the light-emitting element of this embodiment, light emission in a high luminance region can be obtained. Thus, current density can be kept low, and an element having a long lifetime can be realized. Further, a voltage drop due to resistance of an electrode material can be reduced; accordingly, in application to lighting, uniform light emission in a large area can be obtained. Moreover, a light-emitting device which can be driven at low voltage with low power consumption can be achieved.

Furthermore, by making emission colors of the EL layers different, light having a desired color can be obtained from the light-emitting element as a whole. For example, the emission colors of first and second EL layers are complementary in a light-emitting element having the two EL layers, so that so that the light-emitting element can be made to emit white light as a whole. Note that the term "complementary" means color relationship in which an achromatic color is obtained when colors are mixed. That is, emission of white light can be obtained by mixture of light emission from substances whose emission colors are complementary colors.

Further, the same can be applied to a light-emitting element having three EL layers. For example, the light-emitting element as a whole can emit white light when the emission color of the first EL layer is red, the emission color of the second EL layer is green, and the emission color of the third EL layer is blue.

Note that the structure described in this embodiment can be combined with any of the structures described in Embodiments 1 to 3 as appropriate.

(Embodiment 5)

In Embodiment 5, as one embodiment of the present invention, a passive matrix light-emitting device and an active matrix light-emitting device each of which is a light-emitting device fabricated using a light-emitting element will be described.

FIGS. 4A to 4D and FIG. 5 illustrate examples of the passive matrix light-emitting device.

In the passive-matrix (also called simple-matrix) light-emitting device, a plurality of anodes arranged in stripes (in stripe form) is provided to intersect at right angles with a plurality of cathodes arranged in stripes. At their intersections, a light-emitting layer is interposed. Thus, light is emitted from a pixel at the intersection of an anode which is selected (to which a voltage is applied) and a cathode which is selected.

Figure 4A:
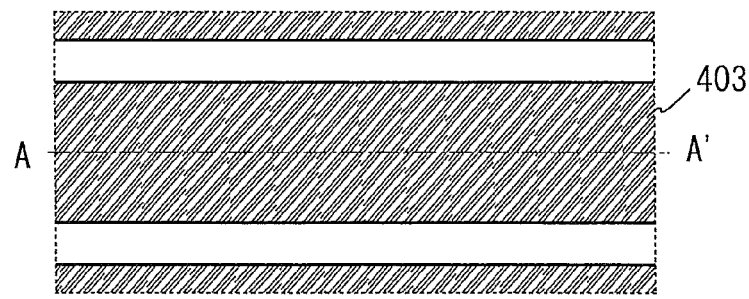
FIGS. 4A to 4D illustrate a passive matrix light-emitting device.
Figure 4B:
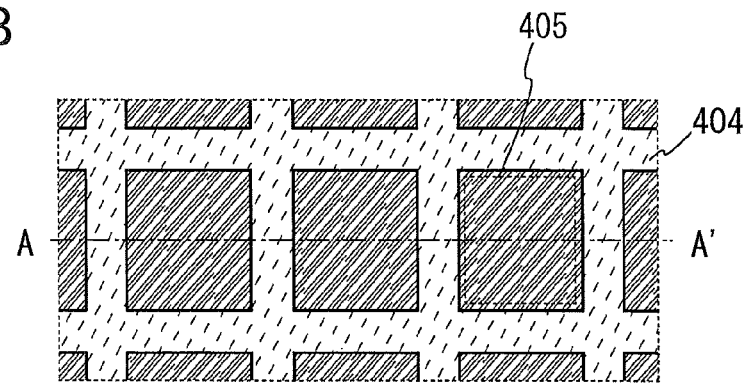
Figure 4C:
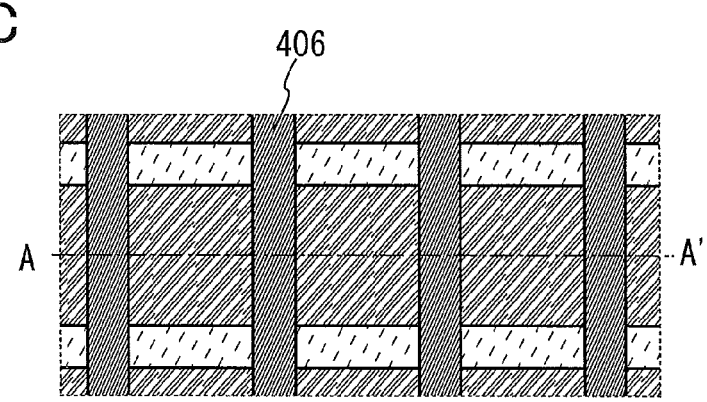
Figure 4D:
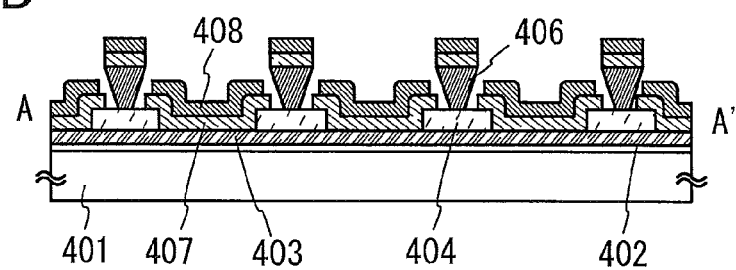

FIGS. 4A to 4C are top views of a pixel portion before sealing. FIG. 4D is a cross-sectional view taken along the chain line A-A' in FIGS. 4A to 4C.

Over a substrate 401, an insulating layer 402 is formed as a base insulating layer. Note that the base insulating layer is not necessarily formed if not needed. Over the insulating layer 402, a plurality of first electrodes 403 is arranged in stripes at regular intervals (FIG. 4A).

In addition, partition 404 having openings corresponding to the pixels is provided over the first electrodes 403. The partition 404 having the openings is formed with an insulating material, such as a photosensitive material or a nonphotosensitive organic material (polyimide, acrylic, polyamide, polyimide amide, resist, or benzocyclobutene) or a SOG film (e.g., a $SiO_x$ film containing an alkyl group). Note that openings 405 corresponding to the pixels serve as light-emitting regions (FIG. 4B).

Over the partition 404 having the openings, a plurality of reversely tapered partitions 406 which are parallel to each other is provided to intersect with the first electrodes 403 (FIG. 4C). The reversely tapered partitions 406 are formed in such a way that, according to a photolithography method, a positive photosensitive resin, an unexposed portion of which serves as a pattern, is used and the amount of exposed light or the length of development time is adjusted so that a lower portion of the pattern is etched more.

After the reversely tapered partitions 406 are formed as illustrated in FIG. 4C, an EL layer 407 and a second electrode 408 are sequentially formed as illustrated in FIG. 4D. The sum of the heights of the partition 404 having the openings and the reversely tapered partition 406 is set to exceed the sum of the thicknesses of the EL layer 407 and the second electrode 408. Consequently, as illustrated in FIG. 4D, a plurality of divided regions each including the EL layer 407 and the second electrode 408 is formed. Note that the plurality of divided regions is electrically isolated from one another.

The second electrodes 408 are electrodes that extend in the direction in which they intersect with the first electrodes 403 and that are arranged in stripes to be parallel to one another. Although a part of the EL layer 407 and a part of a conductive layer for forming the second electrode 408 are formed even over the reversely tapered partition 406, these parts are isolated from the EL layer 407 and the second electrodes 408.

Note that there is no limitation on the first electrode 403 and the second electrode 408 in this embodiment as far as one of them is an anode and the other is a cathode. Further, the stack structure of the EL layer 407 can be adjusted as appropriate depending on the polarities of the electrodes.

Further, if necessary, a sealing material such as a sealing can or a glass substrate may be attached to the substrate 401 to perform sealing with an adhesive such as a sealant so that a light-emitting element is placed in the sealed space. This can prevents deterioration of the light-emitting element. Note that the sealed space may be filled with a filler or a dry inert gas. Further, a desiccant or the like may be put between the substrate and the sealing material to prevent deterioration of the light-emitting element due to moisture or the like. The desiccant removes a minute amount of moisture, thereby achieving sufficient desiccation. The desiccant can be a substance that absorbs moisture by chemical adsorption, such as an oxide of an alkaline-earth metal typified by calcium oxide or barium oxide. As a desiccant other than the above, a substance that adsorbs moisture by physical adsorption, such as zeolite or silica gel, may be used.

Figure 5:
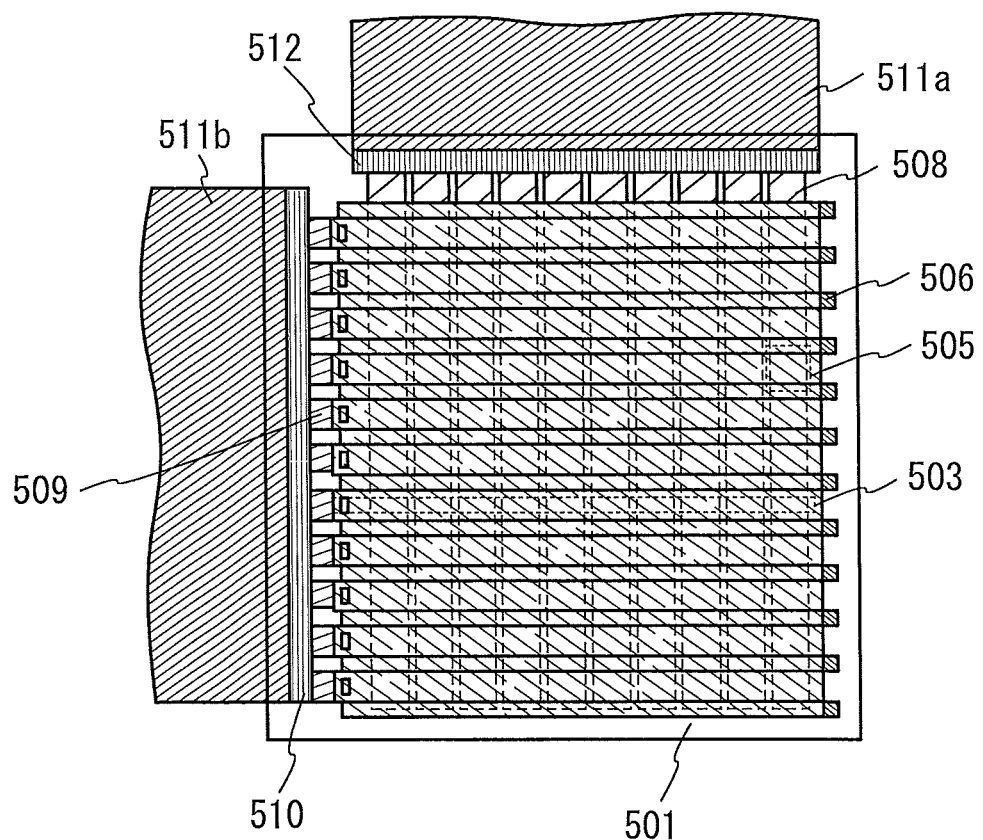
FIG. 5 illustrates a passive-matrix light-emitting device.

FIG. 5 is a top view of the passive matrix light-emitting device illustrated in FIGS. 4A to 4D, on which an FPC and the like are mounted.

In FIG. 5, scan lines and data lines intersect at right angles in the pixel portion for displaying images.

Here, the first electrode 403 in FIGS. 4A to 4D corresponds to a scan line 503 in FIG. 5, the second electrode 408 in FIGS. 4A to 4D corresponds to a data line 508 in FIG. 5, and the reversely tapered partition 406 corresponds to a partition 506. The EL layer 407 in FIGS. 4A to 4D is interposed between the data lines 508 and the scan lines 503, and an intersection indicated as a region 505 corresponds to one pixel.

Note that the scanning lines 503 are electrically connected at their ends to connection wirings 509, and the connection wirings 509 are connected to an FPC 511b via an input terminal 510. In addition, the data lines are connected to an FPC 511a via an input terminal 512.

If necessary, an optical film such a polarizing plate, a circularly polarizing plate (including an elliptically polarizing plate), a retardation plate (a quarter-wave plate or a half-wave plate), and a color filter may be provided as appropriate on a surface through which light is emitted. The polarizing plate or the circularly polarizing plate may be provided with an anti-reflection film. For example, anti-glare treatment by which reflected light can be diffused by projections and depressions on the surface so as to reduce the glare can be performed.

Note that, although FIG. 5 illustrates an example in which a driver circuit is not provided over the substrate 501, an IC chip including a driver circuit may be mounted on the substrate 501.

When the IC chip is mounted, in the peripheral (outside) region of the pixel portion, ICs, in which a driver circuit for transmitting a signal to the pixel portion is formed, are mounted on the data line side and/or the scan line side by a COG method. As the mounting technique other than the COG method, a TCP or a wire bonding method may be used. The TCP is obtained by mounting an IC on a TAB tape in such a way that the TAB tape is connected to a wiring over an element formation substrate and the IC is mounted. The ICs on the data line side and the scan line side may be formed using a silicon substrate, or may be obtained by formation of a driver circuit with a TFT over a glass substrate, a quartz substrate, or a plastic substrate.

Figure 6A:
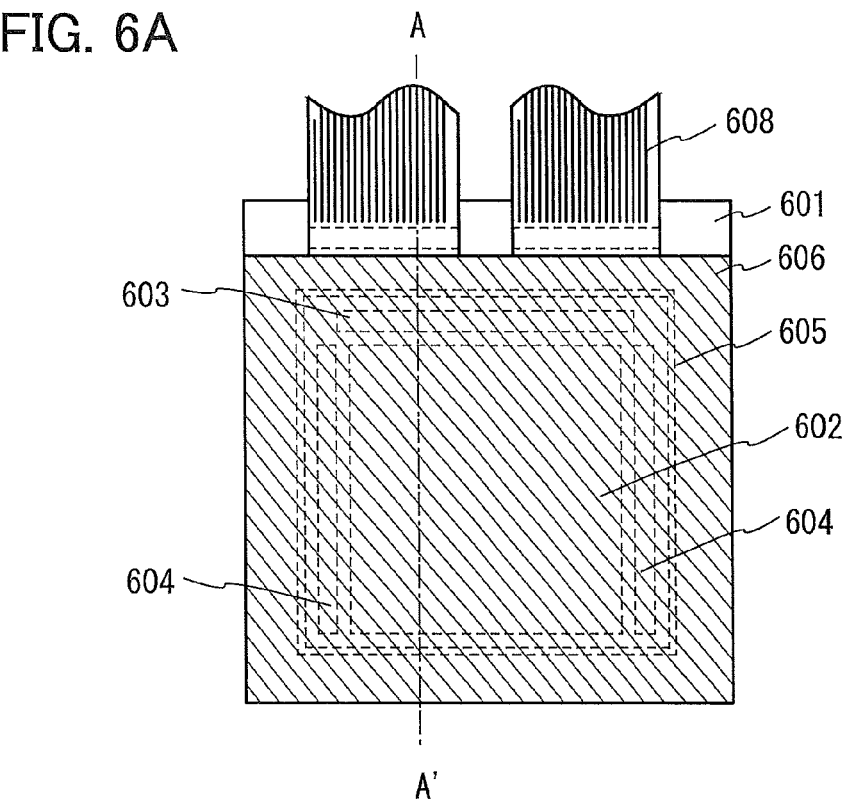
FIGS. 6A and 6B illustrate an active matrix light-emitting device.
Figure 6B:
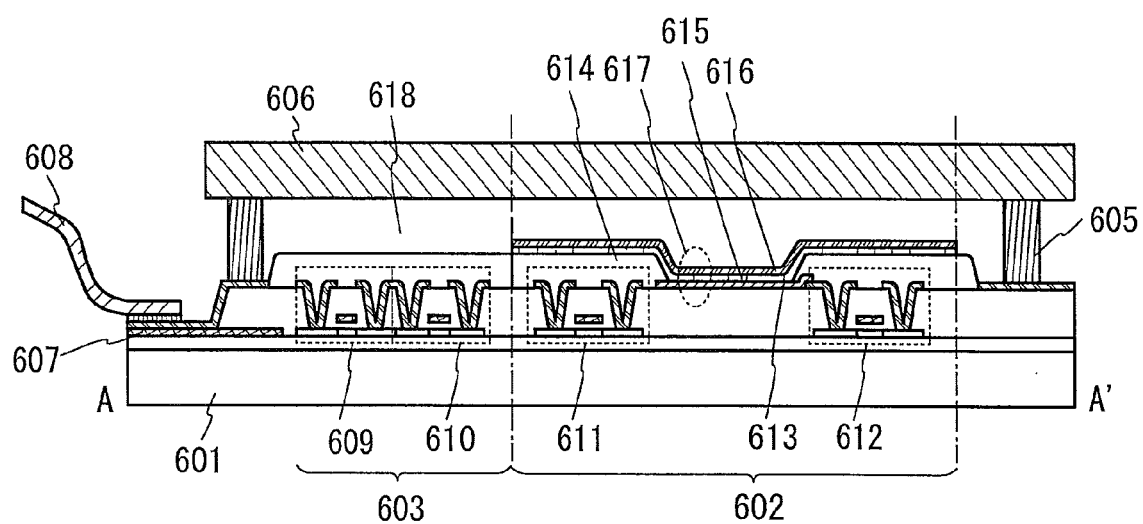

Next, an example of an active-matrix light-emitting device will be described with reference to FIGS. 6A and 6B. Note that FIG. 6A is a top view illustrating the light-emitting device and FIG. 6B is a cross-sectional view taken along the chain line A-A' in FIG. 6A. The active matrix light-emitting device according to this embodiment includes a pixel portion 602 provided over an element substrate 601, a driver circuit portion (a source driver circuit) 603, and a driver circuit portion (a gate driver circuit) 604. The pixel portion 602, the driver circuit portion 603, and the driver circuit portion 604 are sealed between the element substrate 601 and the sealing substrate 606 by the sealing material 605.

In addition, over the element substrate 601, a lead wiring 607 for connecting an external input terminal, through which signals (e.g., a video signal, a clock signal, a start signal, and a reset signal) or a potential from the outside is transmitted to the driver circuit portion 603 and the driver circuit portion 604, is provided. Here, an example in which an FPC (flexible printed circuit) 608 is provided as the external input terminal is described. Although only the FPC is illustrated here, a printed wiring board (PWB) may be attached to this FPC. The light-emitting device in this specification includes not only a light-emitting device itself but also a light-emitting device provided with an FPC or a PWB.

Next, a cross-sectional structure will be described with reference to FIG. 6B. The driver circuit portion and the pixel portion are formed over the element substrate 601, and here the driver circuit portion 603 which is the source driver circuit and the pixel portion 602 are illustrated.

As an example of the driver circuit portion 603, a CMOS circuit which is a combination of an n-channel TFT 609 and a p-channel TFT 610 is formed. Note that the driver circuit portion may be formed with various types of circuits such as CMOS circuits, PMOS circuits, or NMOS circuits. Although a driver integrated type in which the driver circuit is formed over the substrate is illustrated in this embodiment, the driver circuit may not necessarily be formed over the substrate, and the driver circuit can be formed outside, not over the substrate.

The pixel portion 602 includes a plurality of pixels each of which includes a switching TFT 611, a current control TFT 612, and an anode 613 electrically connected to a wiring (a source electrode or a drain electrode) of the current control TFT 612. Note that an insulator 614 is formed to cover an end portion of the anode 613. Here, the insulator 614 is formed using a positive photosensitive acrylic resin.

The insulator 614 is preferably formed so as to have a curved surface with curvature at an upper end portion or a lower end portion thereof in order to obtain favorable coverage by a film which is to be stacked over the insulator 614. For example, in the case where a positive photosensitive acrylic resin is used as a material of the insulator 614, the insulator 614 is preferably formed so as to have a curved surface with a curvature radius (0.2 μm to 3 μm) at the upper end portion. For the insulator 614, either a negative photosensitive material that becomes insoluble in an etchant by light irradiation or a positive photosensitive material that becomes soluble in an etchant by light irradiation can be used, and without limitation to an organic compound, either an organic compound or an inorganic compound such as silicon oxide or silicon oxynitride can be used.

An EL layer 615 and a cathode 616 are stacked over the anode 613. Note that when an ITO film is used as the anode 613, and a stacked film of a titanium nitride film and a film containing aluminum as its main component or a stacked film of a titanium nitride film, a film containing aluminum as its main component, and a titanium nitride film is used as the wiring of the current controlling TFT 612 which is connected to the anode 613, resistance of the wiring is low and favorable ohmic contact with the ITO film can be obtained. Note that, although not illustrated here, the cathode 616 is electrically connected to the FPC 608 which is an external input terminal.

Note that in the EL layer 615, at least a light-emitting layer is provided, and in addition to the light-emitting layer, a hole-injection layer, a hole-transport layer, an electron-transport layer, and an electron-injection layer are provided as appropriate. A light-emitting element 617 has a stacked structure of the anode 613, the EL layer 615, and the cathode 616.

Although the cross-sectional view of FIG. 6B illustrates only one light-emitting element 617, a plurality of light-emitting elements is arranged in matrix in the pixel portion 602. Light-emitting elements which emit three-color (R, G, and B) light are selectively formed in the pixel portion 602, so that a light-emitting device capable of full color display can be formed. Alternatively, a light-emitting device capable of full color display may be obtained by being combined with color filters.

Further, the sealing substrate 606 is attached to the element substrate 601 with the sealing material 605, so that the light-emitting element 617 is provided in a space 618 enclosed by the element substrate 601, the sealing substrate 606, and the sealing material 605. The space 618 may be filled with an inert gas (such as nitrogen or argon), or the sealing material 605.

Note that an epoxy-based resin is preferably used as the sealing material 605. Such a material preferably allows as little moisture and oxygen as possible to penetrate. As a material used for the sealing substrate 606, a plastic substrate formed of FRP (fiberglass-reinforced plastics), PVF (polyvinyl fluoride), polyester, acrylic, or the like can be used other than a glass substrate or a quartz substrate.

As described above, the active matrix light-emitting device can be obtained.

Note that the structure described in this embodiment can be combined with any of the structures described in Embodiments 1 to 4 as appropriate.

(Embodiment 6)

In Embodiment 6, with reference to FIGS. 7A to 7E and FIG. 8, description is given of examples of a variety of electronic devices and lighting devices that are completed by using a light-emitting device which is one embodiment of the present invention.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and a lighting device are illustrated in FIGS. 7A to 7E.

Figure 7A:
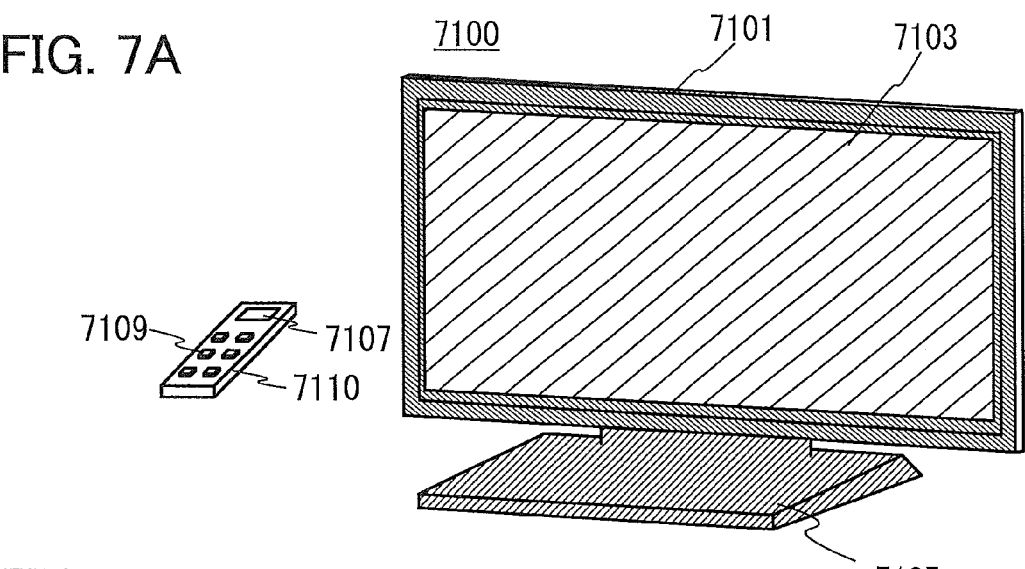
FIGS. 7A to 7E illustrate electronic devices.

FIG. 7A illustrates an example of a television device. In the television device 7100, a display portion 7103 is incorporated into a housing 7101. The display portion 7103 is capable of displaying images, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 7B:
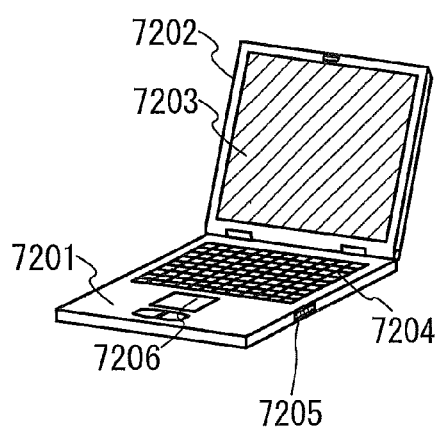

FIG. 7B illustrates a computer having a main body 7201, a housing 7202, a display portion 7203, a keyboard 7204, an external connecting port 7205, a pointing device 7206, and the like. This computer is manufactured by using a light-emitting device for the display portion 7203.

Figure 7C:
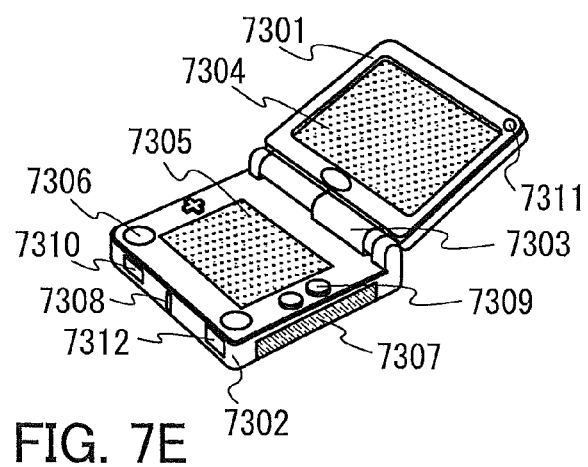

FIG. 7C illustrates a portable game machine having two housings, a housing 7301 and a housing 7302, which are connected with a joint portion 7303 so that the portable game machine can be opened or folded. A display portion 7304 is incorporated into the housing 7301 and a display portion 7305 is incorporated into the housing 7302. In addition, the portable game machine illustrated in FIG. 7C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable games machine is not limited to the above as far as a light-emitting device can be used for at least either the display portion 7304 or the display portion 7305, or both, and may include other accessories arbitrarily. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above.

Figure 7D:
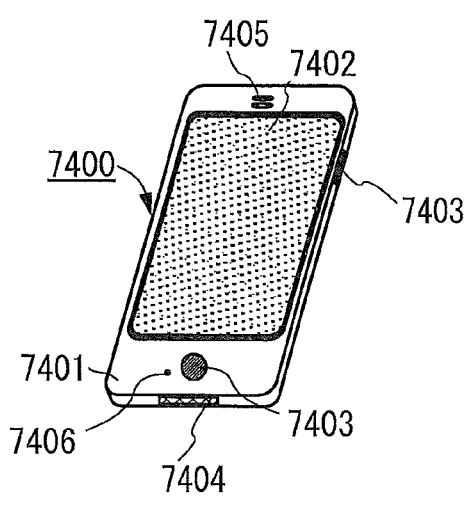

FIG. 7D illustrates an example of a cellular phone. The cellular phone 7400 is provided with operation buttons 7403, an external connection port 7404, a speaker 7405, a microphone 7406, and the like, in addition to a display portion 7402 incorporated into a housing 7401. Note that the cellular phone 7400 is manufactured using a light-emitting device for the display portion 7402.

When the display portion 7402 of the cellular phone 7400 illustrated in FIG. 7D is touched with a finger or the like, data can be input into the cellular phone 7400. Further, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a text input mode mainly for inputting text is selected for the display portion 7402 so that text displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on kinds of images displayed on the display portion 7402. For example, when a signal for an image displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, so that personal authentication can be performed. Furthermore, by provision of a backlight or a sensing light source emitting a near-infrared light for the display portion, an image of a finger vein, a palm vein, or the like can also be taken.

Figure 7E:
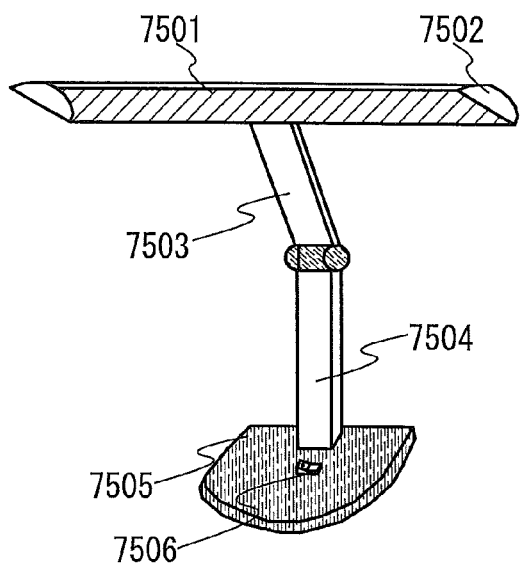

FIG. 7E illustrates a desk lamp including a lighting portion 7501, a shade 7502, an adjustable arm 7503, a support 7504, a base 7505, and a power supply 7506. The desk lamp is manufactured using a light-emitting device for the lighting portion 7501. Note that the "lighting device" also encompasses ceiling lights, wall lights, and the like.

FIG. 8 illustrates an example in which a light-emitting device is used for an interior lighting device 801. Since the light-emitting device can have a larger area, it can be used as a lighting device having a large area. Furthermore, the light-emitting device can be used as a roll-type lighting device 802. As illustrated in FIG. 8, a desk lamp 803 described with reference to FIG. 7E may be used together in a room provided with the interior lighting device 801.

In the above-described manner, electronic devices or lighting devices can be obtained by application of a light-emitting device. Application range of the light-emitting device is so broad that the light-emitting device can be applied to electronic devices in a variety of fields.

Note that the structure described in this embodiment can be combined with any of the structures described in Embodiments 1 to 5 as appropriate.

EXAMPLE 1

Synthesis Example 1

This example specifically illustrates a synthesis example of tris[5-methyl-4-phenyl-3-(5-pyridyl)-4H-1,2,4-triazolato]iridium(III) (abbreviation: [Ir(Mpytz)$_3$]), the organometallic complex represented by the structural formula (100) in Embodiment 1 which is one embodiment of the present invention. A structure of [Ir(Mpytz)$_3$] is shown below.

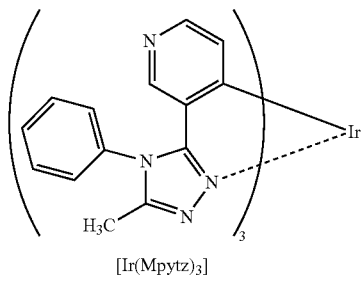

[Ir(Mpytz)$_3$]

Step 1: Synthesis of 3-Methyl-4-phenyl-5-(3-pyridyl)-4H-1,2,4-triazole (abbreviation: HMpytz)

First, into a 100-mL three-neck flask were placed 3.64 g of N-[1-(ethylsulfanyl)ethylidene]aniline, 20 mL of 1-butanol, and 2.78 g of nicotinic acid hydrazide, and the mixture was stirred at 130° C. for 22 hours. After the stirring, this reaction solution was concentrated under reduced pressure to give an oily substance. This oily substance was washed with ethyl acetate, and subjected to suction filtration to give a solid. This solid was purified by alumina column chromatography using ethyl acetate as a developing solvent. The obtained fraction was concentrated to give a solid. This solid was washed with a mixed solvent of ethyl acetate and hexane, so that 3-methyl-4-phenyl-5-(3-pyridyl)-4H-1,2,4-triazole (abbreviation: HMpytz) was obtained (a white solid, 42% yield). The synthesis scheme of Step 1 is illustrated in the following (a-1).

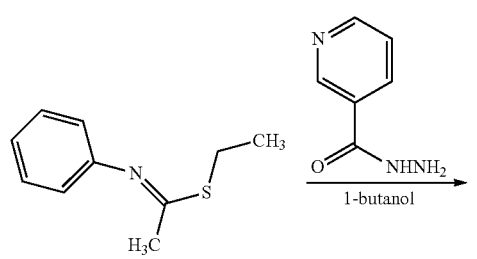

(a-1)

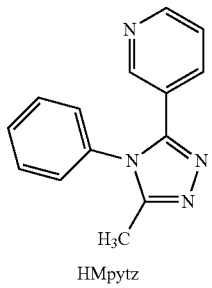

HMpytz

Step 2: Synthesis of Tris[5-methyl-4-phenyl-3-(5-pyridyl)-4H-1,2,4-triazolato]iridium(III) (abbreviation: [Ir(Mpytz)$_3$]

Next, into a reaction container provided with a three-way cock were placed 1.01 g of the ligand HMpytz obtained in the above Step 1 and 0.42 g of tris(acetylacetonato)iridium (III), and the air in the reaction container was replaced with argon. Then, the mixture was heated at 245° C. for 48 hours to be reacted. The reactant was dissolved in dichloromethane, and this solution was suction-filtered with layers of Celite (produced by Wako Pure Chemical Industries, Ltd., Catalog No. 531-16855) and silica gel placed on filter paper. The solvent of the obtained filtrate was distilled off, and the residue was washed with acetone and then with ethyl acetate. The solid after the washing was recrystallized from a mixed solvent of ethanol and hexane, so that the substance which was the object of the synthesis was obtained as a yellow powder in 1% yield. The synthesis scheme is illustrated in the following (b-1).

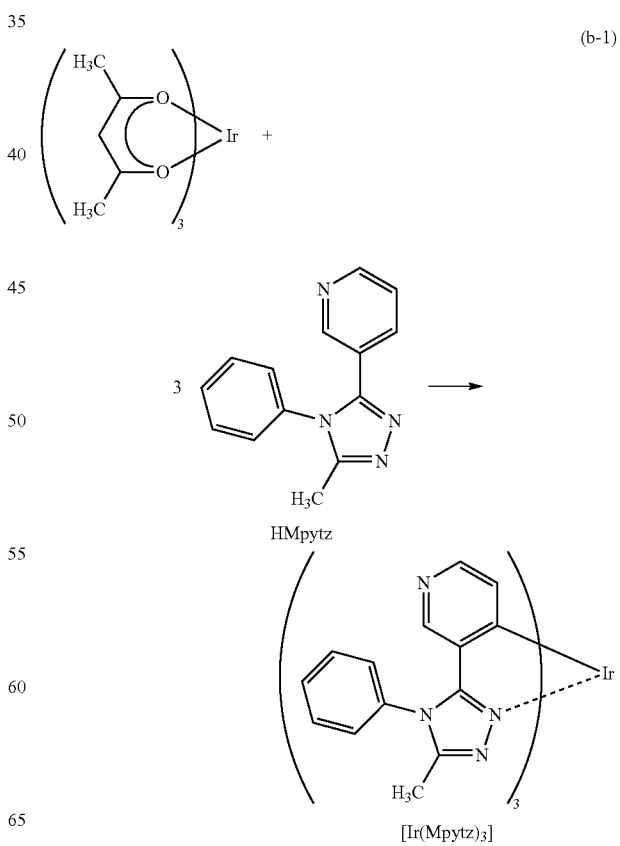

(b-1)

Figure 2:
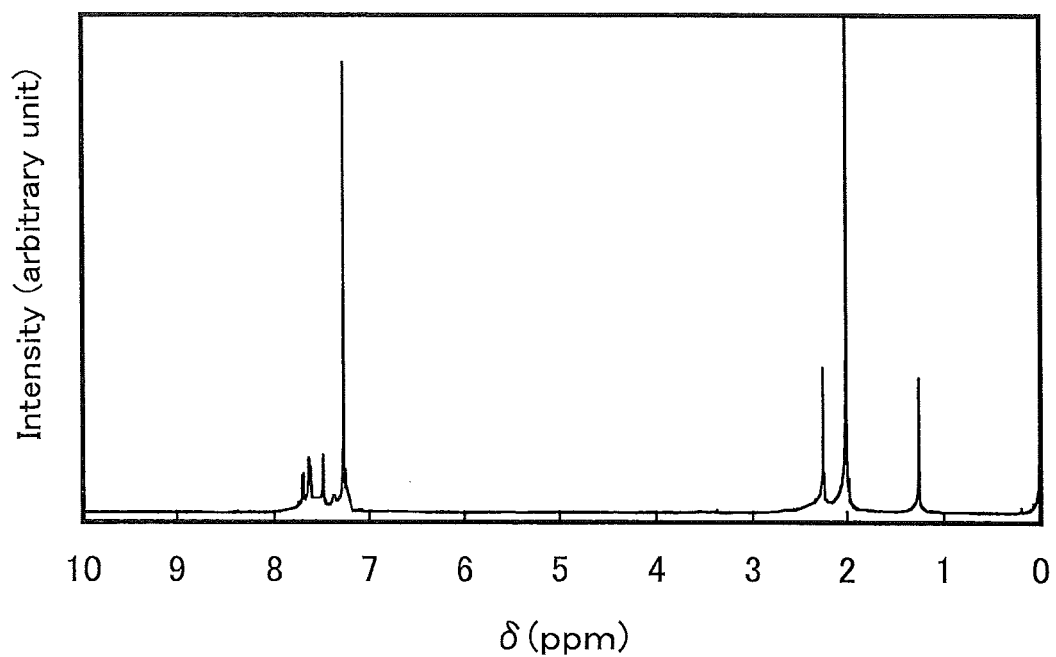
FIG. 2 shows a $^1$H NMR chart of an organometallic complex represented by a structural formula (100).

Analysis results by nuclear magnetic resonance ($^1$H NMR) spectroscopy of the yellow powder obtained in the above Step 2 are shown below. In addition, the $^1$H NMR chart is shown in FIG. 2. These results revealed that [Ir(Mpytz)$_3$], the above-described organometallic complex represented by the structural formula (100) which is one embodiment of the present invention, was obtained in Synthesis Example 1.

$^1$H-NMR. δ (CDCl$_3$): 2.38 (s, 9H), 7.23 (m, 6H), 7.36 (m, 3H), 7.48 (s, 3H), 7.64 (m, 9H), 7.70 (d, 3H).

Figure 3:
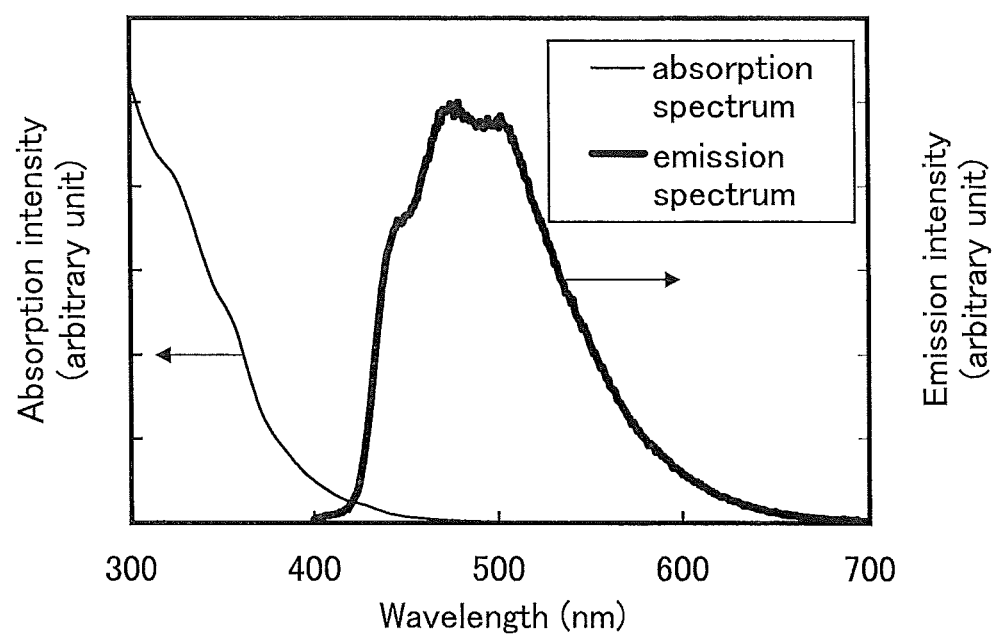
FIG. 3 shows an ultraviolet-visible absorption and emission spectra of the organometallic complex represented by the structural formula (100).

Next, an ultraviolet-visible absorption spectrum (hereinafter, simply referred to as an "absorption spectrum") of [Ir(Mpytz)$_3$] in a dichloromethane solution and an emission spectrum thereof were measured. The measurement of the absorption spectrum was conducted at room temperature, for which an ultraviolet-visible light spectrophotometer (V550 type manufactured by Japan Spectroscopy Corporation) was used and the dichloromethane solution was put in a quartz cell. In addition, the measurement of the emission spectrum was conducted at room temperature, for which a fluorescence spectrophotometer (FS920 manufactured by Hamamatsu Photonics Corporation) was used and the degassed dichloromethane solution was put in a quartz cell. Measurement results of the obtained absorption and emission spectra are shown in FIG. 3. The horizontal axis represents wavelength (nm), and the vertical axis represents absorption intensity (arbitrary unit) and emission intensity (arbitrary unit). In FIG. 3 where there are two solid lines, the thin line represents the absorption spectrum and the thick line represents the emission spectrum. Note that the absorption spectrum in FIG. 3 is the results obtained in such a way that the absorption spectrum measured by putting only dichloromethane in a quartz cell was subtracted from the absorption spectrum measured by putting the dichloromethane solution in a quartz cell.

As shown in FIG. 3, [Ir(Mpytz)$_3$], the organometallic complex of one embodiment of the present invention, has emission peaks at 475 nm and 500 nm, and light blue emission was observed from the dichloromethane solution.

EXAMPLE 2

Synthesis Example 2

This example gives specifically illustrates a synthesis example of tris[5-isopropyl-3-(6-methyl-5-pyridyl)-4-phenyl-4H-1,2,4-triazolato]iridium(III) (abbreviation: [Ir(iPrMpytz)$_3$]), the organometallic complex represented by the structural formula (104) in Embodiment 1 which is one embodiment of the present invention. A structure of [Ir(iPrMpytz)$_3$] is shown below.

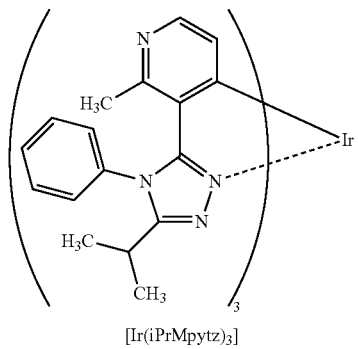

[Ir(iPrMpytz)$_3$]

Step 1: Synthesis of 2-Methylnicotinic Acid Hydrazide

First, 4.12 g of 2-methylnicotinic acid ethyl, 15 mL of 1-butanol, and 1.25 g of hydrazine-hydrate (NH$_2$NH$_2$.H$_2$O) were put into a 100-mL three-neck flask, and the mixture was heated and stirred at 80° C. for 19 hours. After that, 2.38 g of hydrazine-hydrate was further added to the mixture, and the mixture was heated and stirred for 15 hours. After the stirring, the reaction solution was poured into saturated brine, and the mixture was stirred at room temperature for 30 minutes. The organic layer and aqueous layer of this mixture were separated, and organic substances were extracted from the aqueous layer with chloroform. The obtained extract solution and the organic layer were combined, and dried with anhydrous magnesium sulfate added thereto. The resulting mixture after the drying was gravity-filtered, and the filtrate was concentrated to give a solid. The obtained solid was washed with a mixed solvent of ethyl acetate and hexane to give 2-methylnicotinic acid hydrazide (a white solid, 42% yield). The synthesis scheme of Step 1 is illustrated in the following (a-2).

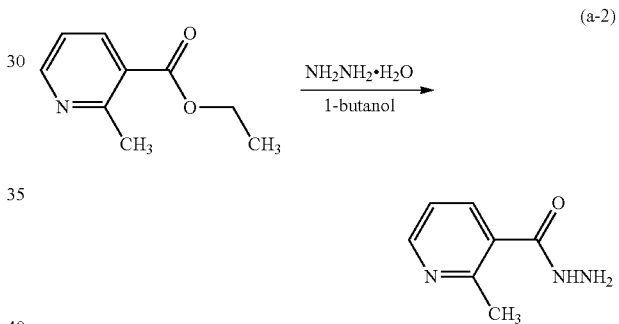

Step 2: Synthesis of 3-Isopropyl-5-(2-methyl-3-pyridyl)-4-phenyl-4H-1,2,4-triazole (abbreviation: HiPrMpytz)

Next, 1.70 g of 2-methylnicotinic acid hydrazide obtained in the above Step 1, 30 mL of 1-butanol, and 2.30 g of N-[1-(ethylsulfanyl)isobutylidene]aniline were put into a 100-mL three-neck flask, and the mixture was heated and stirred at 130° C. for 9 hours. After the stirring, 1.15 g of N-[1-(ethylsulfanyl)isobutylidene]aniline was further added to the mixture, and the mixture was heated and stirred at 130° C. for 18 hours. After that, 1-butanol was distilled off under reduced pressure to give an oily substance. This oily substance was purified by silica gel column chromatography. Ethyl acetate was used as a developing solvent. The obtained fraction was concentrated to give a solid. This solid was further purified by alumina column chromatography. Ethyl acetate was used as a developing solvent. The obtained fraction was concentrated to give a solid. This solid was washed with hexane to give 3-isopropyl-5-(2-methyl-3-pyridyl)-4-phenyl-4H-1,2,4-triazole (abbreviation: HiPrMpytz) (a white solid, 28% yield). The synthesis scheme of Step 2 is illustrated in the following (b-2).

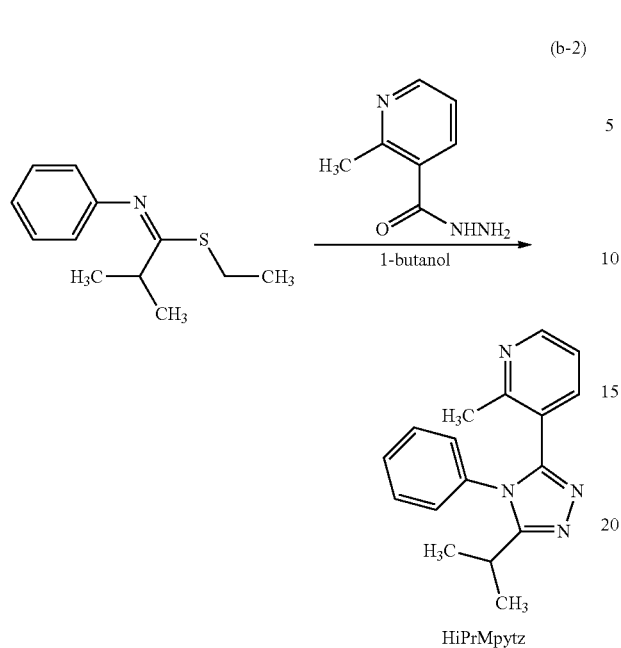

(b-2)

HiPrMpytz

Step 3: Synthesis of Tris[5-isopropyl-3-(6-methyl-5-pyridyl)-4-phenyl-4H-1,2,4-triazolato]iridium(III) (abbreviation: [Ir(iPrMpytz)₃])

Further, 0.87 g of the ligand HiPrMpytz obtained in the above Step 2 and 0.31 g of tris(acetylacetonato)iridium(III) were put into a reaction container provided with a three-way cock, and the air in the reaction container was replaced with argon. Then, the mixture was heated at 250° C. for 49 hours to be reacted. The reactant was dissolved in dichloromethane and purified by silica gel column chromatography. Ethyl acetate was used as a developing solvent. The obtained fraction was concentrated to give a solid. The obtained solid was washed with ethyl acetate, followed by recrystallization from acetone, so that the substance which was the object of the synthesis was obtained as a pale yellow powder in 28% yield. The synthesis scheme is illustrated in the following (c-2).

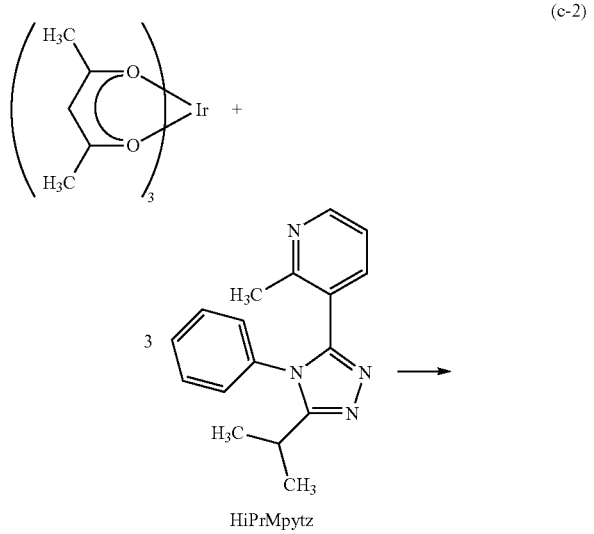

(c-2)

HiPrMpytz

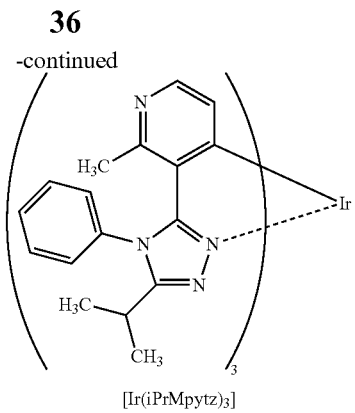

[Ir(iPrMpytz)₃]

Figure 10:
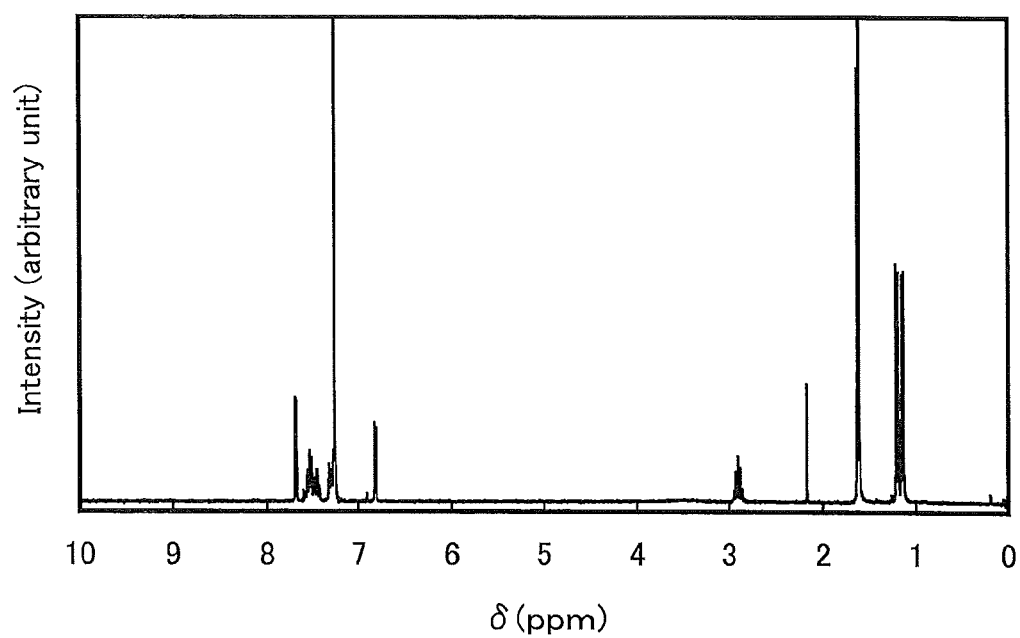
FIG. 10 shows a $^1$H NMR chart of an organometallic complex represented by a structural formula (104).

Analysis results by nuclear magnetic resonance ($^1$H NMR) spectroscopy of the pale yellow powder obtained in the above Step 3 are shown below. In addition, the $^1$H NMR chart is shown in FIG. 10. These results revealed that [Ir(iPrMpytz)₃], the above-described organometallic complex represented by the structural formula (104) which is one embodiment of the present invention, was obtained in Synthesis Example 2.

$^1$H-NMR. δ (CDCl₃): 1.14 (d, 9H), 1.41 (d, 9H), 1.62 (d, 9H), 2.85-2.95 (m, 3H), 6.82 (d, 3H), 7.26-7.32 (m, 6H), 7.43-7.60 (in, 9H), 7.68 (d, 3H).

Figure 11:
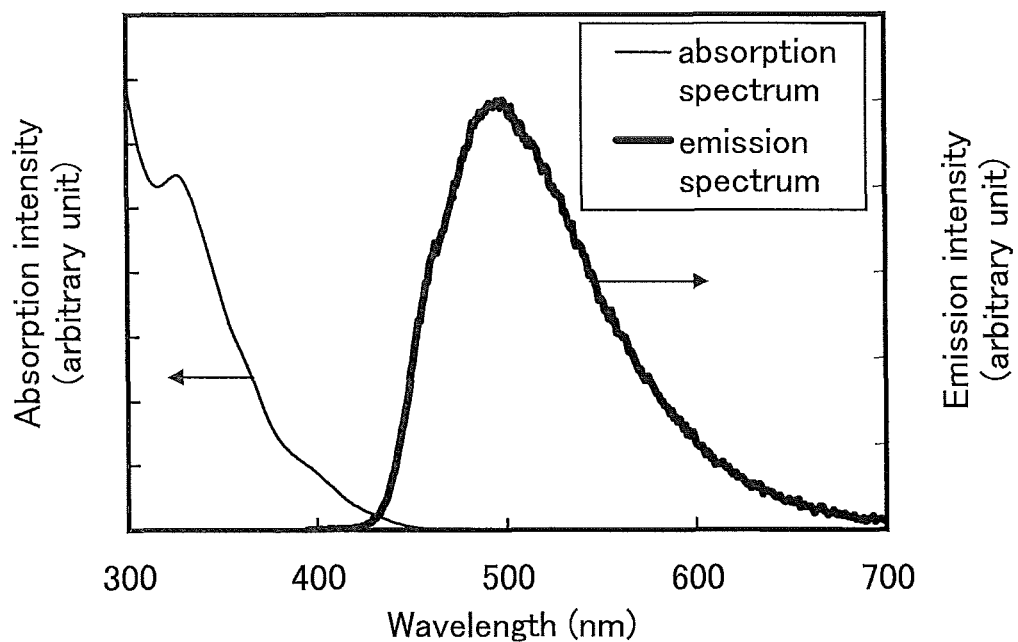
FIG. 11 shows an ultraviolet-visible absorption and emission spectra of the organometallic complex represented by the structural formula (104).

Next, an ultraviolet-visible absorption spectrum (hereinafter, simply referred to as an "absorption spectrum") of [Ir(iPrMpytz)₃] in a dichloromethane solution and an emission spectrum thereof were measured. The measurement of the absorption spectrum was conducted at room temperature, for which an ultraviolet-visible light spectrophotometer (V550 type manufactured by Japan Spectroscopy Corporation) was used and the dichloromethane solution (0.073 mmol/L) was put in a quartz cell. In addition, the measurement of the emission spectrum was conducted at room temperature, for which a fluorescence spectrophotometer (FS920 manufactured by Hamamatsu Photonics Corporation) was used and the degassed dichloromethane solution (0.073 mmol/L) was put in a quartz cell. Measurement results of the obtained absorption and emission spectra are shown in FIG. 11. The horizontal axis represents wavelength (nm), and the vertical axis represents absorption intensity (arbitrary unit) and emission intensity (arbitrary unit). In FIG. 11 where there are two solid lines, the thin line represents the absorption spectrum and the thick line represents the emission spectrum. Note that the absorption spectrum in FIG. 11 is the results obtained in such a way that the absorption spectrum measured by putting only dichloromethane in a quartz cell was subtracted from the absorption spectrum measured by putting the dichloromethane solution (0.073 mmol/L) in a quartz cell.

As shown in FIG. 11, [Ir(iPrMpytz)₃], the organometallic complex of one embodiment of the present invention, has an emission peak at 496 nm, and light blue-green emission was observed from the dichloromethane solution.

EXAMPLE 3

Figure 9:
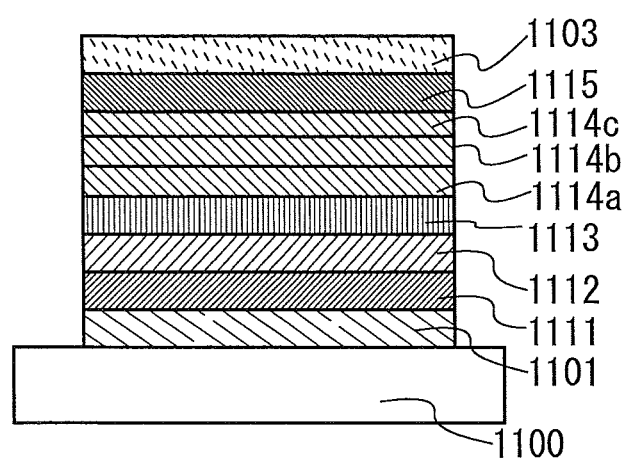
FIG. 9 illustrates light-emitting elements of Examples.

In this example, a light-emitting element in which tris[5-isopropyl-3-(6-methyl-5-pyridyl)-4-phenyl-4H-1,2,4-triazolato]iridium(III) (abbreviation: [Ir(iPrMpytz)₃]) synthesized in Example 2 is used as a light-emitting substance will be described with reference to FIG. 9. Chemical formulae of materials used in this example are shown below.

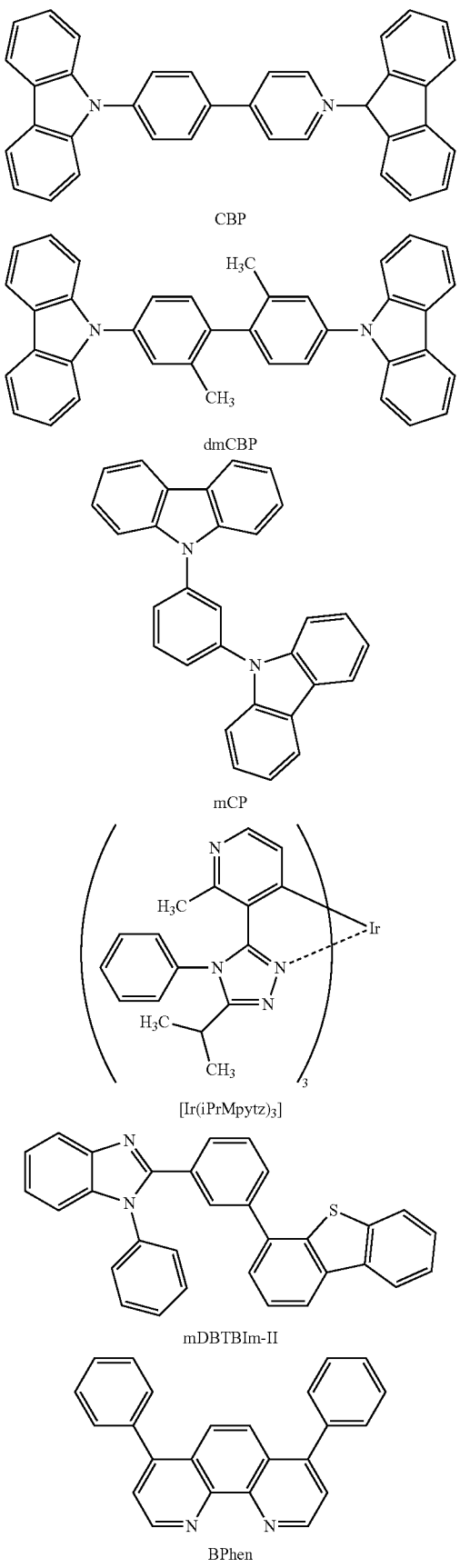

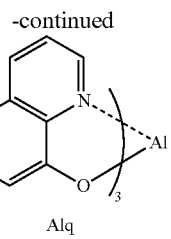

The way in which Light-Emitting Element 1 was fabricated will now be described.

(Light-Emitting Element 1)

First, a film of indium tin oxide containing silicon oxide (ITSO) was formed over a glass substrate 1100 by a sputtering method, so that a first electrode 1101 was formed. Note that its thickness was set to 110 nm and the electrode area was set to 2 mm×2 mm.

Next, in pretreatment for forming the light-emitting element on the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^4$ Pa. Then, 4,4'-di(N-carbazolyl)biphenyl (abbreviation: CBP) and molybdenum(VI) oxide were co-evaporated to form a hole-injection layer 1111 on the first electrode 1101. The thickness of the hole-injection layer 1111 was set to 50 nm, and the weight ratio of CBP to molybdenum(VI) oxide was adjusted to 4:2 (=CBP:molybdenum oxide). Note that the co-evaporation method refers to an evaporation method in which evaporation is carried out from a plurality of evaporation sources at the same time in one treatment chamber.

Next, on the hole-injection layer 1111, a film of 4,4'-bis(9-carbazole)-2,2'-dimethyl-biphenyl (abbreviation: dmCBP) was formed to a thickness of 10 nm to form a hole-transport layer 1112.

Further, 1,3-bis(N-carbazolyl)benzene (abbreviation: mCP) and tris[5-isopropyl-3-(6-methyl-5-pyridyl)-4-phenyl-4H-1,2,4-triazolato]iridium(III) (abbreviation: [Ir(iPrMpytz)$_3$]) synthesized in Example 2 were co-evaporated to form a light-emitting layer 1113 on the hole-transport layer 1112. Here, the weight ratio of mCP to Ir(iPrMpytz)$_3$ was adjusted to 1:0.08 (=mCP: [Ir(iPrMpytz)$_3$]). In addition, the thickness of the light-emitting layer 1113 was set to 30 nm.

Next, on the light-emitting layer 1113, a film of 2-[3-(dibenzothiophen-4-yl)phenyl]-1-phenyl-1H-benzimidazole (abbreviation: mDBTBIm-II) was formed to a thickness of 10 nm to form a first electron-transport layer 1114a.

Further, on the first electron-transport layer 1114a, a film of tris(8-quinolinolato)aluminum(III) (abbreviation: Alq) was formed to a thickness of 10 nm to form a second electron-transport layer 1114b.

Then, a film of bathophenanthroline (abbreviation: BPhen) was formed to a thickness of 15 nm on the second electron-transport layer 1114b, so that the third electron-transport layer 1114c was formed.

Further, on the third electron-transport layer 1114c, lithium fluoride (LiF) was evaporated to a thickness of 1 nm to form an electron-injection layer 1115.

Lastly, aluminum was evaporated to a thickness of 200 nm as a second electrode 1103 functioning as a cathode. Thus, Light-Emitting Element 1 of this example was fabricated.

Note that, in the above evaporation process, evaporation was all performed by a resistance heating method.

Table 1 shows an element structure of Light-Emitting Element 1 obtained as described above.

TABLE 1

| | First electrode | Hole-injection layer | Hole-transport layer | Light-emitting layer |
|---|---|---|---|---|
| Light-Emitting Element 1 | ITSO 110 nm | CBP:MoOx (=4:2) 50 nm | dmCBP 10 nm | mCP:[Ir(iPrMpytz)$_3$] (=1:008) 30 nm |

| First electron-transport layer | Second electron-transport layer | Third electron-transport layer | Electron-injection layer | Second electrode |
|---|---|---|---|---|
| mDBTBIm-II 10 nm | Alq 10 nm | BPhen 15 nm | LiF 1 nm | Al 200 nm |

In a glove box containing a nitrogen atmosphere, Light-Emitting Element 1 was sealed so as not to be exposed to air. Then, operation characteristics of Light-Emitting Element 1 were measured. Note that the measurements were carried out at room temperature (in the atmosphere kept at 25° C.).

Figure 12:
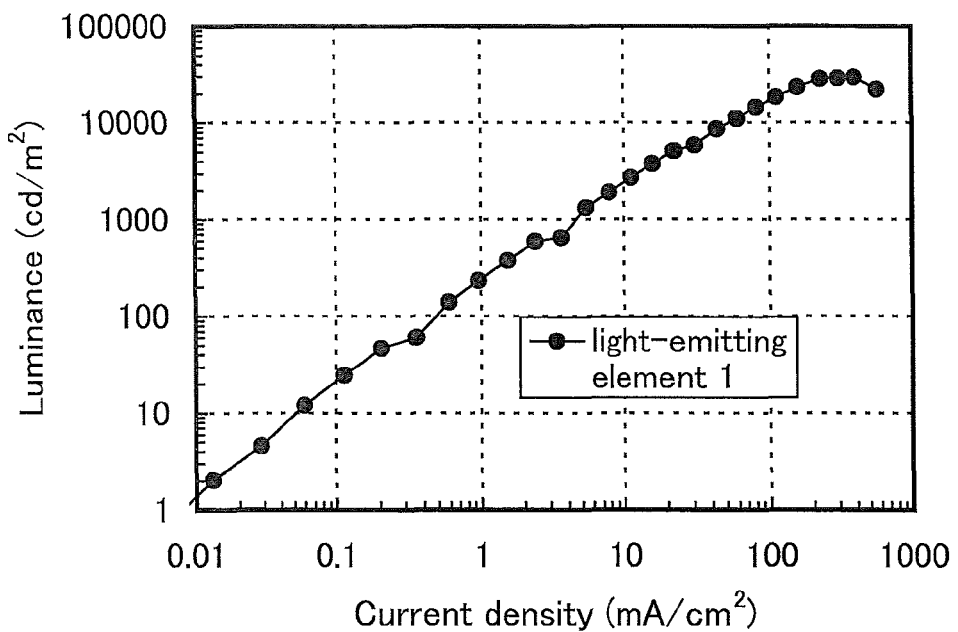
FIG. 12 shows luminance versus current density characteristics of a light-emitting element which is one embodiment of the present invention.
Figure 13:
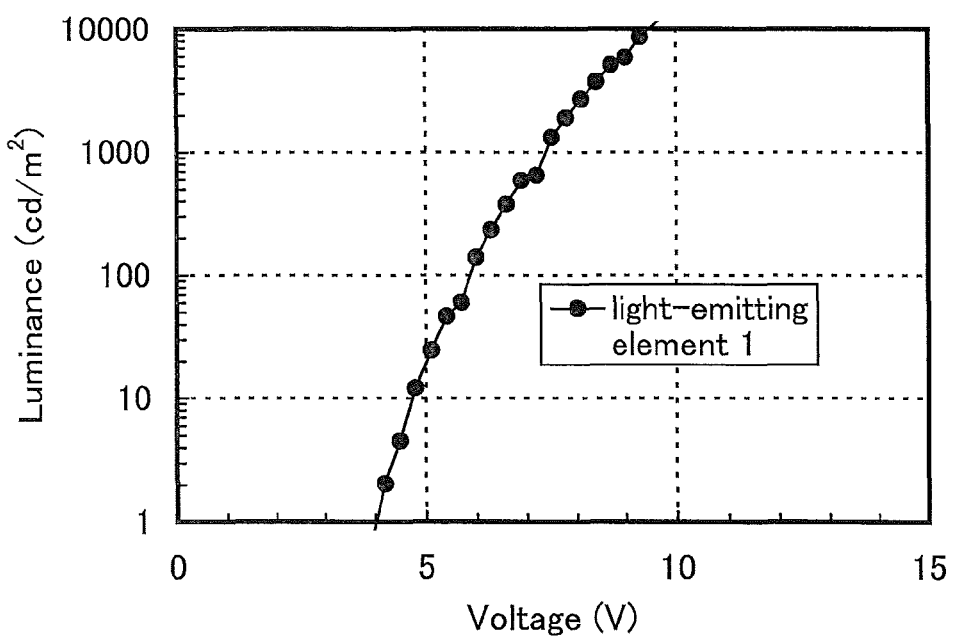
FIG. 13 shows luminance versus voltage characteristics of the light-emitting element which is one embodiment of the present invention.
Figure 14:
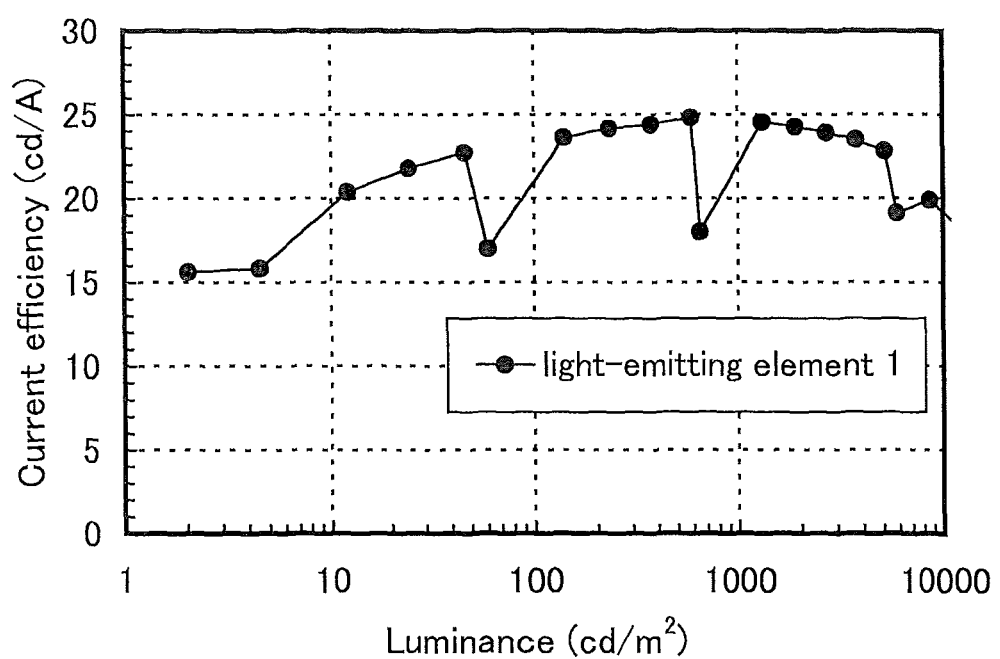
FIG. 14 shows current efficiency versus luminance characteristics of the light-emitting element which is one embodiment of the present invention.

FIG. 12 shows the luminance versus current density characteristics of Light-Emitting Element 1. In FIG. 12, the horizontal axis represents current density (mA/cm$^2$) and the vertical axis represents luminance (cd/m$^2$). In addition, FIG. 13 shows the luminance versus voltage characteristics. In FIG. 13, the horizontal axis represents voltage (V) and the vertical axis represents luminance (cd/m$^2$). FIG. 14 shows the current efficiency versus luminance characteristics. In FIG. 14, the horizontal axis represents luminance (cd/m$^2$) and the vertical axis represents current efficiency (cd/A). Further, Table 2 shows the voltage (V), current density (mA/cm$^2$), CIE chromaticity coordinates (x, y), current efficiency (cd/A), and external quantum efficiency (%) of Light-Emitting Element 1 at a luminance of 1300 cd/m$^2$.

TABLE 2

| | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 1 | 7.5 | 5.4 | 0.23, 0.35 | 1300 | 25 | 11 |

Figure 15:
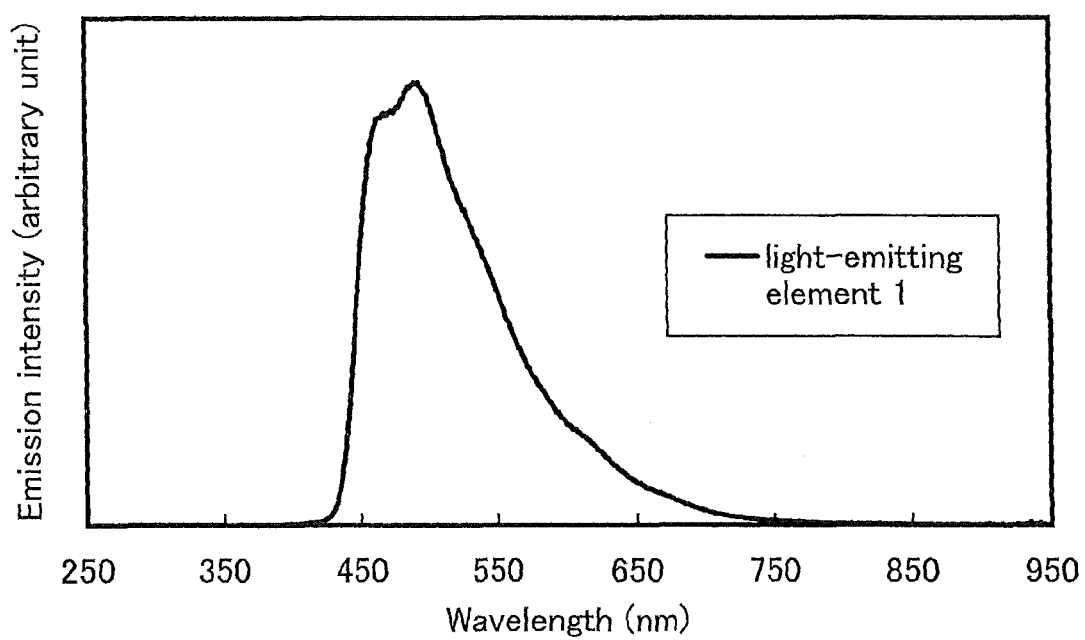
FIG. 15 shows an emission spectrum of the light-emitting element which is one embodiment of the present invention.

FIG. 15 shows the emission spectrum obtained when a current was supplied to the light-emitting element at a current density of 0.1 mA/cm$^2$. As shown in FIG. 15, the emission spectrum of Light-Emitting Element 1 has a peak at 490 nm. Further, as shown in Table 2, the CIE chromaticity coordinates of Light-Emitting Element 1 (x, y) were (0.23, 0.35) at a luminance of 1300 cd/m$^2$. Light-Emitting Element 1 was found to provide light emission from [Ir(iPrMpytz)$_3$]. It was shown that a light-emitting element using an organometallic complex of one embodiment of the present invention enabled efficient emission of short-wavelength light.

EXAMPLE 4

In this example, a light-emitting element in which [Ir(iPrMpytz)$_3$], the organometallic complex of one embodiment of the present invention synthesized in Example 2, was used as a light-emitting substance will be described with reference to FIG. 9. The materials used in this example are illustrated in the above Example, and therefore chemical formulae thereof are omitted here.

The way in which Light-Emitting Element 2 of this example was fabricated will now be described.
(Light-Emitting Element 2)

First, an ITSO film was formed over the glass substrate 1100 by a sputtering method, so that the first electrode 1101 was formed. Note that its thickness was set to 110 nm and the electrode area was set to 2 mm×2 mm.

Next, in pretreatment for forming the light-emitting element on the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately 10$^4$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about 10$^{-4}$ Pa. Then, CBP and molybdenum(VI) oxide were co-evaporated to form the hole-injection layer 1111 on the first electrode 1101. The thickness of the hole-injection layer 1111 was set to 50 nm, and the weight ratio of CBP to molybdenum(VI) oxide was adjusted to 4:2 (=CBP:molybdenum oxide). Note that the co-evaporation method refers to an evaporation method in which evaporation is carried out from a plurality of evaporation sources at the same time in one treatment chamber.

Next, a dmCBP film was formed to a thickness of 10 nm on the hole-injection layer 1111, so that the hole-transport layer 1112 was formed.

Further, CBP and [Ir(iPrMpytz)$_3$] synthesized in Example 2 were co-evaporated to form the light-emitting layer 1113 on the hole-transport layer 1112. Here, the weight ratio of CBP to [Ir(iPrMpytz)$_3$] and FIrpic was adjusted to 1:0.08 (=CBP: [Ir(iPrMpytz)$_3$]). The thickness of the light-emitting layer 1113 was set to 30 nm.

Next, a film of mDBTBIm-II was formed to a thickness of 10 nm on the light-emitting layer 1113, so that the first electron-transport layer 1114a was formed.

Then, on the first electron-transport layer 1114a, an Alq film was formed to a thickness of 10 nm to form the second electron-transport layer 1114b.

Then, on the second electron-transport layer 1114b, a BPhen film was formed to a thickness of 15 nm to form a third electron-transport layer 1114c.

Further, on the third electron-transport layer 1114c, LiF was evaporated to a thickness of 1 nm to form the electron-injection layer 1115.

Lastly, aluminum was evaporated to a thickness of 200 nm as a second electrode 1103 functioning as a cathode. Thus, Light-Emitting Element 2 of this example was fabricated.

Note that, in the above evaporation process, evaporation was all performed by a resistance heating method.

Table 3 shows an element structure of Light-Emitting Element 2 obtained as described above.

TABLE 3

| | First electrode | Hole-injection layer | Hole-transport layer | Light-emitting layer |
|---|---|---|---|---|
| Light-Emitting Element 2 | ITSO 110 nm | CBP:MoOx (=4:2) 50 nm | dmCBP 10 nm | CBP:[Ir(iPrMpytz)$_3$] (=1:.008) 30 nm |

| First electron-transport layer | Second electron-transport layer | Third electron-transport layer | Electron-injection layer | Second electrode |
|---|---|---|---|---|
| mDBTBIm-II 10 nm | Alq 10 nm | BPhen 15 nm | LiF 1 nm | Al 200 nm |

In a glove box containing a nitrogen atmosphere, Light-Emitting Element 2 was sealed so as not to be exposed to air. Then, operation characteristics of Light-Emitting Element 2 were measured. Note that the measurements were carried out at room temperature (in the atmosphere kept at 25° C.).

Figure 16:
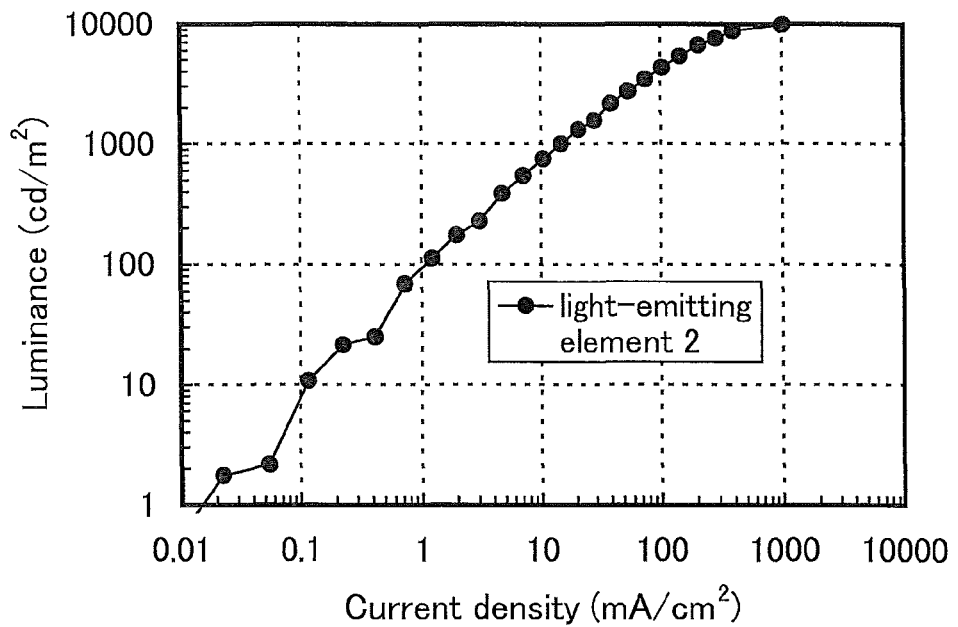
FIG. 16 shows luminance versus current density characteristics of a light-emitting element which is one embodiment of the present invention.
Figure 17:
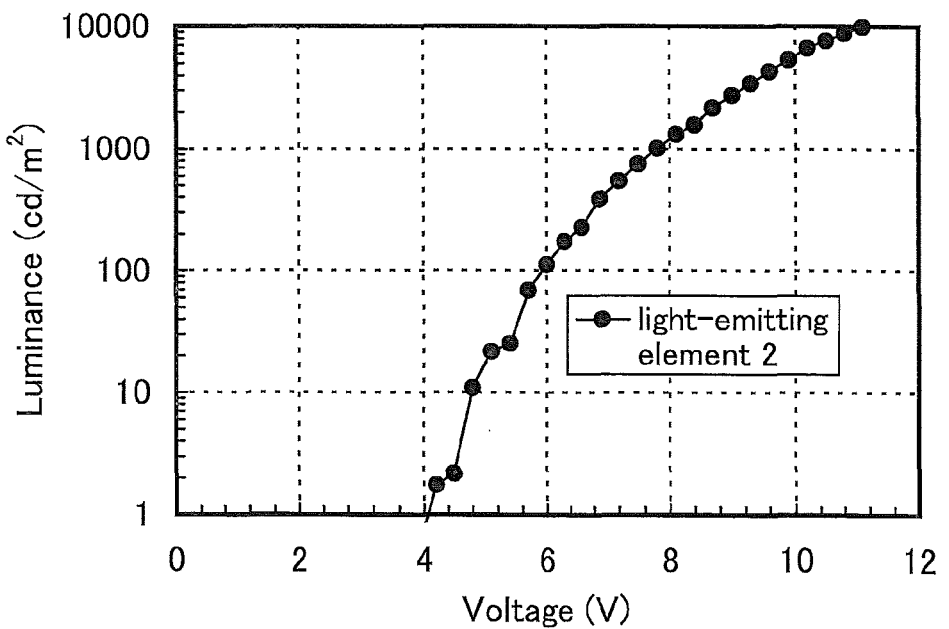
FIG. 17 shows luminance versus voltage characteristics of the light-emitting element which is one embodiment of the present invention.
Figure 18:
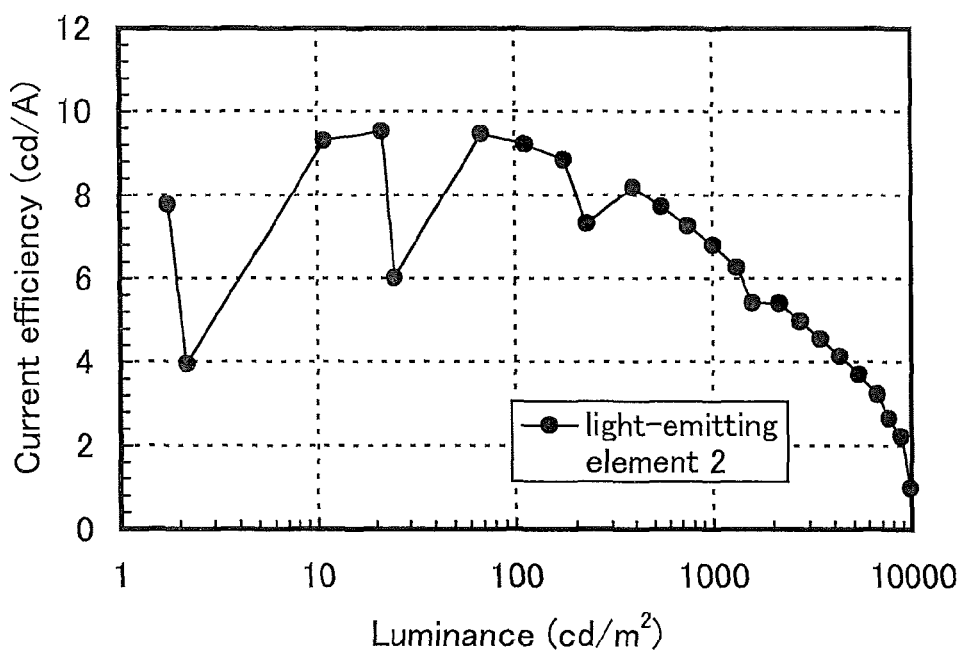
FIG. 18 shows current efficiency versus luminance characteristics of the light-emitting element which is one embodiment of the present invention.

FIG. 16 shows the luminance versus current density characteristics of Light-Emitting Element 2. In FIG. 16, the horizontal axis represents current density (mA/cm$^2$) and the vertical axis represents luminance (cd/m$^2$). In addition, FIG. 17 shows the luminance versus voltage characteristics. In FIG. 17, the horizontal axis represents voltage (V) and the vertical axis represents luminance (cd/m$^2$). FIG. 18 shows the current efficiency versus luminance characteristics. In FIG. 18, the horizontal axis represents luminance (cd/m$^2$) and the vertical axis represents current efficiency (cd/A). Further, Table 4 shows the voltage (V), current density (mA/cm$^2$), CIE chromaticity coordinates (x, y), current efficiency (cd/A), and external quantum efficiency (%) of Light-Emitting Element 2 at a luminance of 1000 cd/m$^2$.

TABLE 4

| | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 2 | 7.8 | 15 | 0.27, 0.39 | 1000 | 6.8 | 2.9 |

Figure 19:
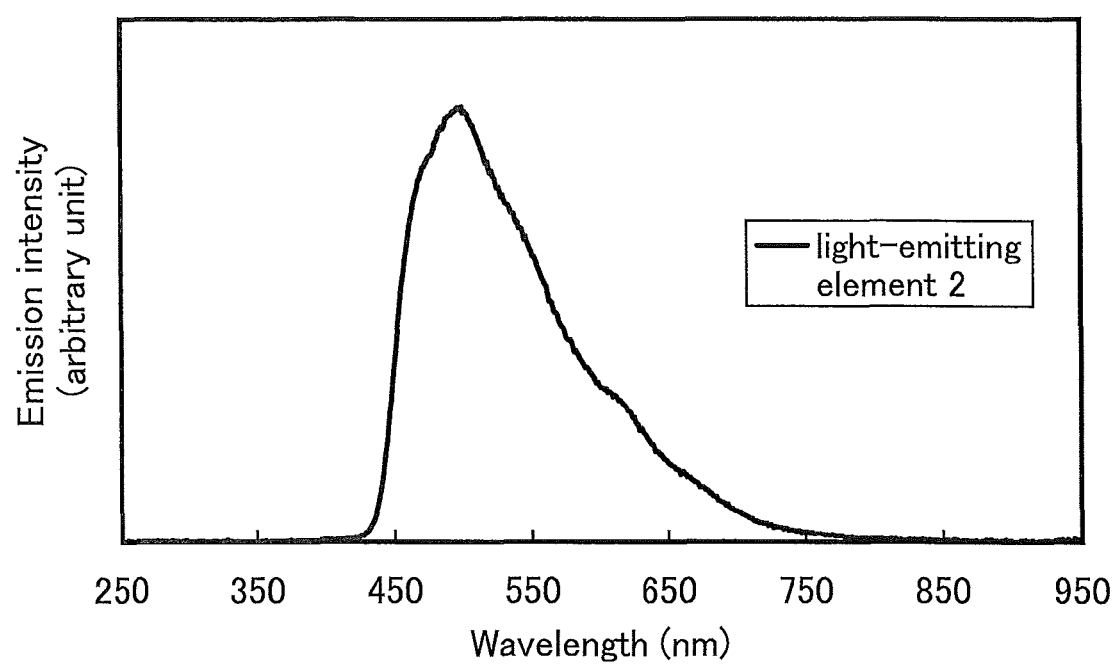
FIG. 19 shows an emission spectrum of the light-emitting element which is one embodiment of the present invention.

FIG. 19 shows the emission spectrum obtained when a current was supplied to the light-emitting element at a current density of 0.1 mA/cm$^2$. As shown in FIG. 19, the emission spectrum of Light-Emitting Element 2 has a peak at 500 nm. Further, as shown in Table 4, the CIE chromaticity coordinates of Light-Emitting Element 2 (x, y) were (0.27, 0.39) at a luminance of 1000 cd/m$^2$. Light-Emitting Element 2 was found to provide light emission from [Ir(iPrMpytz)$_3$]. It was shown that a light-emitting element using an organometallic complex of one embodiment of the present invention enabled efficient emission of short-wavelength light.

REFERENCE EXAMPLE 1

A method of synthesizing 2-[3-(dibenzothiophen-4-yl)phenyl]-1-phenyl-1H-benzimidazole (abbreviation: mDBTBIm-II) used in the above Examples will be described. A structure of mDBTBIm-II is shown below.

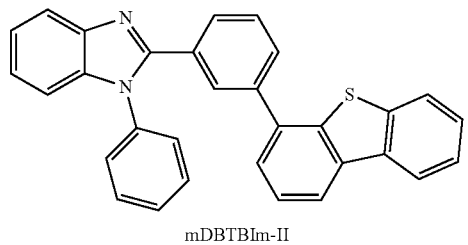 [SMILES: c1ccc(-n2c(-c3cccc(-c4cccc5c4sc4ccccc45)c3)nc3ccccc32)cc1]

mDBTBIm-II

Synthesis of 2-[3-(Dibenzothiophen-4-yl)phenyl]-1-phenyl-1H-benzimidazole (abbreviation: mDBTBIm-II)

A scheme of the synthesis of mDBTBIm-II is shown in (x-1).

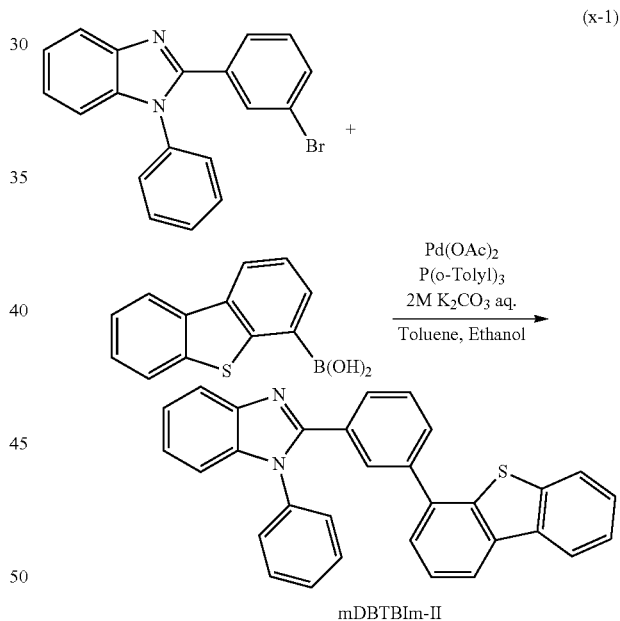

(x-1)

mDBTBIm-II

Into a 50-mL three-neck flask were put 1.2 g (3.3 mmol) of 2-(3-bromophenyl)-1-phenyl-1H-benzimidazole, 0.8 g (3.3 mmol) of dibenzothiophen-4-boronic acid, and 50 mg (0.2 mmol) of tri(ortho-tolyl)phosphine. The air in the flask was replaced with nitrogen. To this mixture were added 3.3 mL of a 2.0 mmol/L aqueous solution of potassium carbonate, 12 mL of toluene, and 4 mL of ethanol. Under reduced pressure, this mixture was stirred to be degassed. Then, 7.4 mg (33 μmol) of palladium(II) acetate was added to this mixture, and the mixture was stirred at 80° C. for 6 hours under a nitrogen stream.

After a predetermined time, organic substances were extracted from the aqueous layer of the obtained mixture with toluene. The obtained extract solution combined with the organic layer was washed with saturated brine, and then drying over magnesium sulfate was performed. This mixture was separated by gravity filtration, and the filtrate was concentrated to give an oily substance. This oily substance was purified by silica gel column chromatography. The silica gel column chromatography was carried out using toluene as a developing solvent. The obtained fraction was concentrated to give an oily substance. This oily substance was purified by high performance liquid chromatography. The high performance liquid column chromatography was performed using chloroform as a developing solvent. The obtained fraction was concentrated to give an oily substance. This oily substance was recrystallized from a mixed solvent of toluene and hexane, so that the substance which was the object of the synthesis was obtained as 0.8 g of a pale yellow powder in 51% yield.

By a train sublimation method, 0.8 g of the obtained pale yellow powder was purified. In the purification, the pale yellow powder was heated at 215° C. under a pressure of 3.0 Pa with a flow rate of argon gas of 5 mL/min. After the purification, 0.6 g of a white powder of the substance which was the object of the synthesis was obtained in a yield of 82%.

This compound was identified as mDBTBIm-II by a nuclear magnetic resonance (NMR) spectroscopy.

$^1$H NMR data of the obtained compound are as follows:
$^1$H NMR (CDCl$_3$, 300 MHz): δ (ppm)=7.23-7.60 (m, 13H), 7.71-7.82 (m, 3H), 7.90-7.92 (m, 2H), 8.10-8.17 (m, 2H).

This application is based on Japanese Patent Application serial no. 2010-169868 filed with the Japan Patent Office on Jul. 28, 2010, the entire contents of which are hereby incorporated by reference.

What is claimed is:

1. An organometallic complex represented by formula (100)

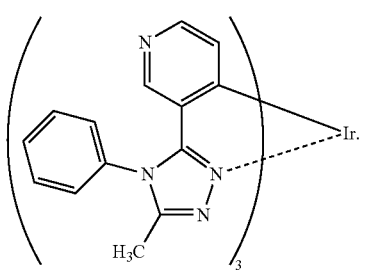

2. An organometallic complex represented by formula (104)

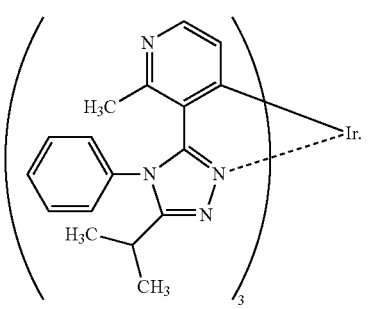

3. An organometallic complex represented by any one of formulae (101), (102), (103), and (105)

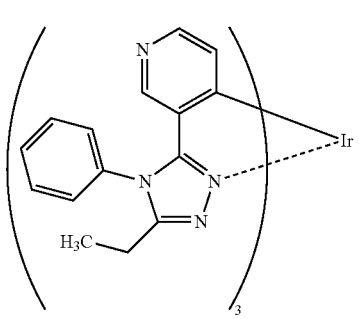

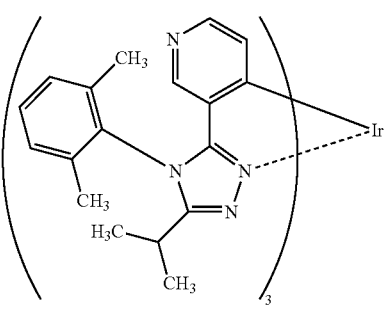

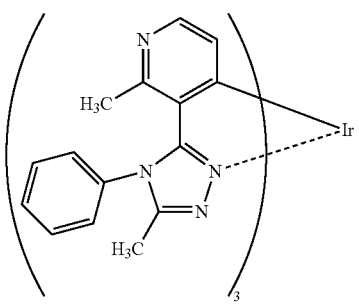

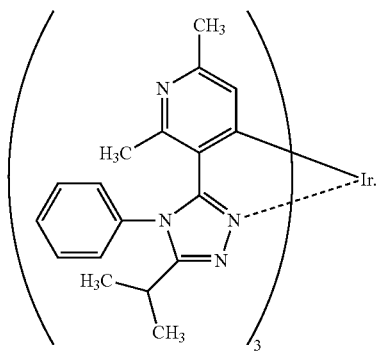

4. A light-emitting element comprising:
a light-emitting layer between a pair of electrodes,
wherein the light-emitting layer includes the organometallic complex according to claim 1.

5. A light-emitting element comprising:
a light-emitting layer between a pair of electrodes,
wherein the light-emitting layer includes the organometallic complex according to claim 2.

6. A light-emitting element comprising:
a light-emitting layer between a pair of electrodes,
wherein the light-emitting layer includes the organometallic complex according to claim 3.

7. A light-emitting device comprising the light-emitting element according to claim 4.

8. A light-emitting device comprising the light-emitting element according to claim 5.

9. A light-emitting device comprising the light-emitting element according to claim 6.

10. An electronic device comprising the light-emitting device according to claim 7.

11. An electronic device comprising the light-emitting device according to claim 8.

12. An electronic device comprising the light-emitting device according to claim 9.

13. A lighting device comprising the light-emitting device according to claim 7.

14. A lighting device comprising the light-emitting device according to claim 8.

15. A lighting device comprising the light-emitting device according to claim 9.

* * * * *

UNITED STATES PATENT AND TRADEMARK OFFICE
CERTIFICATE OF CORRECTION

PATENT NO. : 9,461,252 B2
APPLICATION NO. : 14/447906
DATED : October 4, 2016
INVENTOR(S) : Hideko Inoue et al.

It is certified that error appears in the above-identified patent and that said Letters Patent is hereby corrected as shown below:

In the Specification

Column 1, Line 50; Change "fainted" to --formed--.

Column 17, Line 59; Change "(-vinyltriphenylamine)" to --(4-vinyltriphenylamine)--.

Column 22, Line 35; Change "DCJTB)," to --DCJTI),--.

Column 34, Line 6; Change "($NH_2NH_2.H_2O$)" to --($NH_2NH_2 \cdot H_2O$)--.

Column 36, Line 22; Change "fonnula" to --formula--.

Column 36, Line 27; Change "(in, 9H)," to --(m, 9H),--.

Column 38, Line 36; Change "$10^4$ Pa." to --$10^{-4}$ Pa.--.

Column 40, Line 29; Change "$10^4$ Pa," to --$10^{-4}$ Pa,--.

Signed and Sealed this
Seventh Day of March, 2017

Michelle K. Lee
*Director of the United States Patent and Trademark Office*

CERTIFICATE OF CORRECTION (continued)
U.S. Pat. No. 9,461,252 B2

In the Claims

Column 43, Lines 37 to 48, formula (100), Claim 1; Change

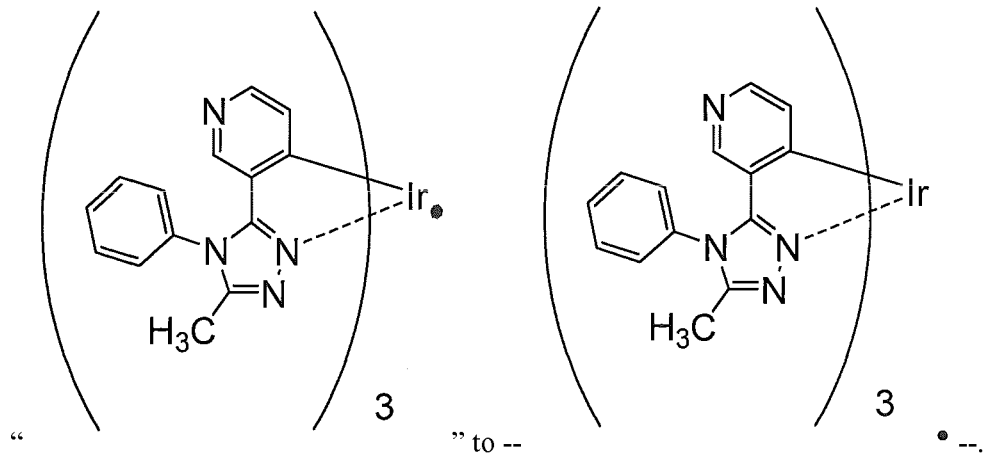

" to --

Column 43, Lines 53 to 66, formula (104), Claim 2; Change

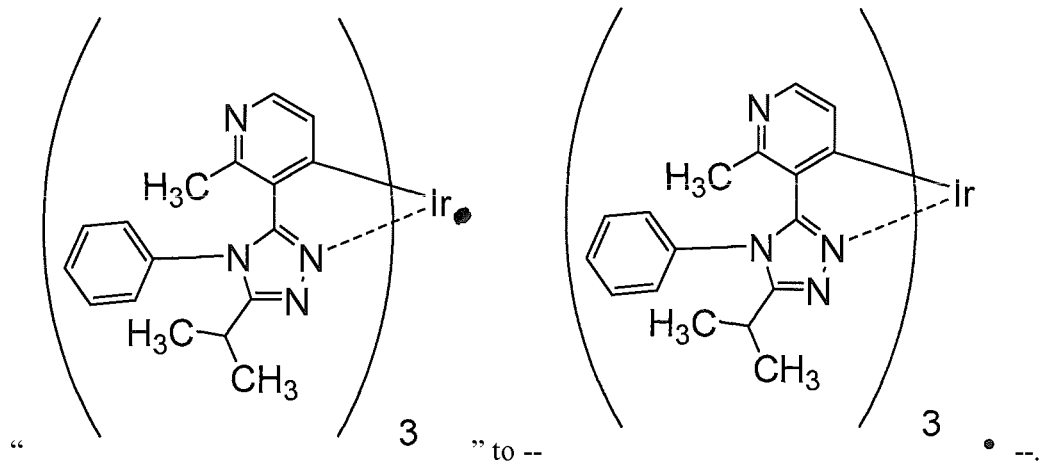

" to --

Column 44, Lines 41 to 54, formula (105), Claim 3; Change

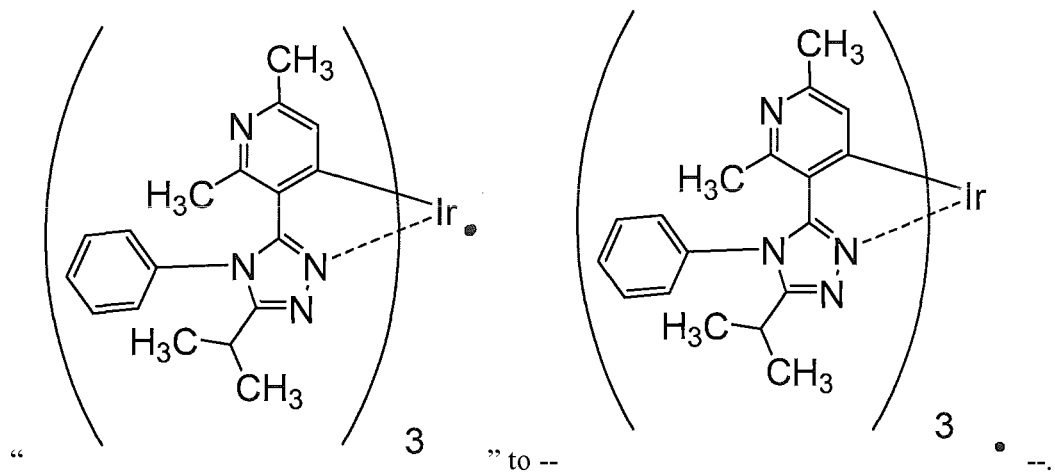

" to --.